(12) United States Patent
Millary et al.

(10) Patent No.: US 10,872,691 B2
(45) Date of Patent: Dec. 22, 2020

(54) POINT OF SERVICE TRANSACTION MANAGEMENT FOR SERVICE FACILITIES

(71) Applicant: ImageVision.net, Inc., Mechanicsburg, PA (US)

(72) Inventors: David Millary, Dillsburg, PA (US); Ken Blessing, Mechanicsburg, PA (US); Brian Clementoni, Harrisburg, PA (US)

(73) Assignee: IMAGEVISION.NET, LLC, Mechanicsburg, PA (US)

( * ) Notice: Subject to any disclaimer, the term of this patent is extended or adjusted under 35 U.S.C. 154(b) by 388 days.

(21) Appl. No.: 14/943,726

(22) Filed: Nov. 17, 2015

(65) Prior Publication Data

US 2016/0259897 A1    Sep. 8, 2016

Related U.S. Application Data

(63) Continuation of application No. 12/763,419, filed on Apr. 20, 2010, now Pat. No. 9,189,781, which is a
(Continued)

(51) Int. Cl.
| | |
|---|---|
| *G16H 40/20* | (2018.01) |
| *G06Q 20/00* | (2012.01) |
| *G06Q 20/20* | (2012.01) |
| *G06Q 20/28* | (2012.01) |
| *G06Q 30/02* | (2012.01) |

(Continued)

(52) U.S. Cl.
CPC ........... *G16H 40/20* (2018.01); *G06F 19/328* (2013.01); *G06Q 20/00* (2013.01); *G06Q 20/102* (2013.01); *G06Q 20/20* (2013.01); *G06Q 20/202* (2013.01); *G06Q 20/28* (2013.01); *G06Q 30/02* (2013.01); *G06Q 30/04* (2013.01); *G06Q 40/00* (2013.01); *G06Q 40/025* (2013.01); *G06Q 40/04* (2013.01); *G06Q 40/12* (2013.12); *G06Q 50/22* (2013.01);
(Continued)

(58) Field of Classification Search
None
See application file for complete search history.

(56) References Cited

U.S. PATENT DOCUMENTS

| | | | | |
|---|---|---|---|---|
| 6,067,530 A | * | 5/2000 | Brooks, Jr. | .......... G06O 20/206 705/30 |
| 6,496,806 B1 | * | 12/2002 | Horwitz | ............. G06K 17/0029 705/28 |

(Continued)

OTHER PUBLICATIONS

Lowes, R. (2002). Don't let dollars walk out the door. Medical Economics, 79(10), 58-60, 62, 65. Retrieved from http://serach.proquest.com/docview/227738674?accountid=14753 (Year: 2002).*

*Primary Examiner* — Scott A Zare
(74) *Attorney, Agent, or Firm* — Thomas J. McWilliams; Barnes & Thornburg LLP

(57) ABSTRACT

The present invention enables the collection by credit/debit card payment of customer co-pay and self-pay charges via an integrated point-of-service transaction management system and method. The system and method of the present invention may assist health care facilities in the collection of co-pay and self-pay charges at the time service is rendered. The present invention can be implemented anywhere cash, checks, credit cards or debit cards are accepted for payment.

7 Claims, 37 Drawing Sheets

Related U.S. Application Data continuation of application No. 10/719,889, filed on Nov. 21, 2003, now Pat. No. 7,567,925.

(60) Provisional application No. 60/428,977, filed on Nov. 25, 2002, provisional application No. 60/428,311, filed on Nov. 22, 2002.

(51) Int. Cl.
*G06Q 30/04* (2012.01)
*G06Q 40/00* (2012.01)
*G06Q 40/02* (2012.01)
*G06Q 40/04* (2012.01)
*G06Q 50/24* (2012.01)
*G16H 10/60* (2018.01)
*G06Q 20/10* (2012.01)
*G06Q 50/22* (2018.01)
*G06F 19/00* (2018.01)
*G16H 40/00* (2018.01)
*G16H 10/40* (2018.01)

(52) U.S. Cl.
CPC ............ *G06Q 50/24* (2013.01); *G16H 10/40* (2018.01); *G16H 10/60* (2018.01); *G16H 40/00* (2018.01)

(56) References Cited

U.S. PATENT DOCUMENTS

| | | | |
|---|---|---|---|
| 6,571,218 B1* | 5/2003 | Sadler | G06Q 20/20 235/462.01 |
| 6,761,308 B1* | 7/2004 | Hanna | G06Q 20/1085 235/379 |
| 2002/0046057 A1* | 4/2002 | Ross | G06O 20/40 705/43 |
| 2002/0099634 A1* | 7/2002 | Coutts | G06Q 20/1085 705/35 |
| 2004/0068441 A1* | 4/2004 | Werbitt | G06Q 30/06 705/16 |
| 2005/0086140 A1* | 4/2005 | Ireland | G07D 11/30 705/35 |

* cited by examiner

Welcome

Terminal ID: 5

POS System / Process Payment / Patient Search

Patient Search

Last Name:
First Name:
MR Number:
AR Number:

Search

Quick-Pick Recent Registrations

*You have not recently registered a patient.*

FIG. 2

Welcome

POS System / Process Payment / Patient Selection                                    Terminal ID: 5

Search Results

| Last Name | First Name | Street | City | State | Zip |
|---|---|---|---|---|---|
| Doe-1 | Lee | 123 Main St. | Philadelphia | PA | 19135 |
| Doe-1 | Maryellen | 123 Main St. | Philadelphia | PA | 19114 |
| Doe-10 | Kelly | 123 Main St. | Philadelphia | PA | 19124 |
| Doe-100 | Mary | 123 Main St. | Philadelphia | PA | 19149 |
| Doe-1000 | James | 123 Main St. | Philadelphia | PA | 19135 |
| Doe-100016 | William | 123 Main St. | Philadelphia | PA | 19124 |
| Doe-100022 | Amber | 123 Main St. | Philadelphia | PA | 19124 |
| Doe-100026 | James P | 123 Main St. | Philadelphia | PA | 19137 |
| Doe-10004 | Giovanna | 123 Main St. | Trevoso | PA | 19053 |
| Doe-100049 | Jamirah | 123 Main St. | Philadelphia | PA | 19114 |
| Doe-100053 | Jamil | 123 Main St. | Philadelphia | PA | 19124 |
| Doe-100071 | Margaret | 123 Main St. | Trevose | PA | 19053 |
| Doe-100077 | David | 123 Main St. | Philadelphia | PA | 19148 |

Search Again                                     Enter Patient Manually

POS System
Process Payment
Reprint Receipt
Close Terminal
Change Password
Exit

Process Payment
1 Patient Search
2 Patient Selection
3 Payment Entry
4 Payment Collection
5 Print Receipt

Help ?
Select the patient from the list or manually enter one if the patient does not exist in the POS system.

FIG. 3

Welcome

POS System / Process Payment / Payment Entry                          Terminal ID: 5

Payment Entry

Askia Doe- 10453                                   MR # 80788422
123 Main St.                                       WARNING BAD DEBT
Levittown, PA 19054

Charges                                            View Payment History

| Type  | AR Number | Service Date | Amount Due | Payment Amount | Note |
|-------|-----------|--------------|------------|----------------|------|
| Prior | 10498060  | 9/07/2000    | $ 282.27   | $ 282.27       | ▫    |
| Prior | 10526053  | 10/9/2000    | $ 52.47    | $ 52.47        | ▫    |
| Prior | 10612275  | 1/21/2001    | $ 25.00    | $ 15.26        | ▫    |
| Prior | 10745691  | 6/25/2001    | $ 31.08    | $ 0.00         | ▫    |
| Prior | 10985412  | 4/3/2002     | $ 12.70    | $ 0.00         | ▫    |

Add Physician Transaction              Add Hospital Transaction

Total Due: $403.52
                              InitialPayment: $350.00
                              Form of Payment: | Cash       ▸ |  Payment >
                                                 Cash
                                                 Check
                                                 Credit Card
                                                 ATMCard < Select Patient

---

POS System

Process Payment
Reprint Receipt
Close Terminal
Change Password
Exit

Process Payment

1 Patient Search
2 Patient Selection
3 Payment Entry
4 Payment Collection
5 Print Receipt

Help ?

Enter amount to be collected for each transaction, or create active transactions. Payment history shows prior paychecks with the option to void.

FIG. 4

Welcome

POS System / Process Payment / Payment Collection

Payment Collection

| AR Number | Service Date | Service Code | Amount Due | Payment Amount |
|---|---|---|---|---|
| 10498060 | Sep 7 2000 | EUR | $ 282.27 | $ 282.27 |
| 10526053 | Oct 9 2000 | EUR | $ 52.47 | $ 52.47 |
| 10612275 | Jan 21 2001 | EUR | $ 25.00 | $ 25.00 |
| 10745691 | Jun 25 2001 | EUR | $ 31.08 | $ 31.08 |
| 10985412 | Apr 3 2002 | EUR | $ 12.70 | $ 12.70 |

Collect Cash Now

Amount Due: $403.52
Amount Tendered:
Change Due: $0.00

< Re-enter Payment          Confirm Payment >

POS System
Process Payment
Reprint Receipt
Close Terminal
Change Password
Exit

Process Payment
1 Patient Search
2 Patient Selection
3 Payment Entry
4 Payment Collection
5 Print Receipt

Help ?
Process the patient payment or reversal.

FIG. 5A

Payment Collection

POS System / Process Payment / Payment Collection

Terminal ID: 5

| AR Number | Service Date | Service Code | Amount Due | Payment Amount |
|---|---|---|---|---|
| 10498060 | Sep 7 2000 | EUR | $ 282.27 | $ 282.27 |
| 10526053 | Oct 9 2000 | EUR | $ 52.47 | $ 52.47 |
| 10612275 | Jan 21 2001 | EUR | $ 25.00 | $ 25.00 |
| 10745691 | Jun 25 2001 | EUR | $ 31.08 | $ 31.08 |
| 10985412 | Apr 3 2002 | EUR | $ 12.70 | $ 12.70 |

Check Information

Enter Check Number: [            ]

Check Amount: $403.52

< Re-enter Payment                                     Confirm Payment >

POS System
Process Payment
Reprint Receipt
Close Terminal
Change Password
Exit

Process Payment
1 Patient Search
2 Patient Selection
3 Payment Entry
4 Payment Collection
5 Print Receipt

Help ?
Process the patient payment or reversal.

FIG. 5B

Welcome

POS System / Process Payment / Payment Collection                                    Terminal ID

Payment Collection

| AR Number | Service Date | Service Code | Amount Due | Payment Amount |
|-----------|--------------|--------------|------------|----------------|
| 10498060  | Sep 7 2000   | EUR          | $ 282.27   | $ 282.27       |
| 10526053  | Oct 9 2000   | EUR          | $ 52.47    | $ 52.47        |
| 10612275  | Jan 21 2001  | EUR          | $ 25.00    | $ 25.00        |
| 10745691  | Jun 25 2001  | EUR          | $ 31.08    | $ 31.08        |
| 10985412  | Apr 3 2002   | EUR          | $ 12.70    | $ 12.70        |

Confirm the Following

Card Number: **  ** 2265
Expiration Date (mmyy): 0706
Cardholder's First Name: Askia
Last Name: Rumph
Address: 9071 Milcreek Rd #1511
City: Levittown
State: PA
Zip: 19054

FIG. 5C

Patient Access Report

Date From: [06/22/2003] (mm/dd/yyyy)
Date To: [08/22/2003] (mm/dd/yyyy)

[Get Report]

Note: patients listed were not viewed by POS operators.

| Employee Name | Usage | Viewed | Registered |
|---|---|---|---|
| − Gustafson, Jonathan (gus) | | | |
| − Aug 12 2003 | 69.23% | 18 | 26 |
| Patient: Doe-40282, Gerald MR # 00744839 | 60.00% | 9 | 15 |
| Patient: Doe752, john MR # 00893841 | | | |
| Patient: Doe537, Kenneth MR # 00647719 | | | |
| Patient: Doe109584, Ann MR # 00893744 | | | |
| Patient: Doe32929, James MR # 00893935 | | | |
| Patient: Doe763, Judy MR # 00881287 | | | |
| − Aug 4 2003 | 81.82% | 9 | 11 |
| Patient: Doe114167, Tracy MR # 00894032 | | | |
| − Anand, Ajith (aanand) | 100.00% | 3 | 3 |
| Aug 12 2003 | 100.00% | 3 | 3 |
| − Operator, Demo (doperator) | 100.00% | 2 | 2 |
| Jul 10 2003 | 100.00% | 2 | 2 |

FIG. 11

Closed Batches Report

Date From: [9/22/2003] (mm/dd/yyyy)
Date To: [9/22/2003] (mm/dd/yyyy)

[Get Report]

Print

| Batch | Account | Name | Type | Amount |
|---|---|---|---|---|
| 426 | Jonathan (22) | Sep 22 2003 2:10PM | | $2,689.18 |
| | 2 Non-Patient Transactions - Bag #777890 | | | $580.00 |
| | Training | George Burns | Cash | $500.00 |
| | book store | Jonathan Gustafson | Check | $80.00 |
| | 5 Patient Transactions - Bag #777889 | | | $2,109.18 |
| | 24555888 | Luther Doe10590 | Credit Card | $19.18 |
| | 11174182 | Mary Doe-100 | Cash | $40.00 |
| | 24376109 | Tressa Doe11229 | Check | $25.00 |
| | 24411265 | Tressa Doe11229 | Check | $25.00 |
| | 24160304 | Rexford T Doe10573 | Check | $2,000.00 |

FIG. 12

Collection Report

Date From: 06/22/2003 (mm/dd/yyyy)
Date To: 09/22/2003 (mm/dd/yyyy)
Selected Entity: [H]1 ImageVision.net

[C] 1 Methodist                              $44,804.11
        Cash            $43,898.41
        Check              $905.70
[C] 3 ancer                                   $5,694.10
        Cash             $2,394.10
        Check            $3,000.00
        Credit Card        $300.00
[C] 4      University                        $16,089.65
        Cash            $12,203.35
        Check            $2,516.66
        Credit Card      $1,369.64
[C] 5 Philadelphia                           $15,477.25
        ATM Card           $319.00
        Cash             $6,840.81
        Check            $7,296.26
        Credit Card      $1,021.18
[C] 7 Harrisburg                                $222.00
        Cash               $222.00

ATM Card:      $319.00
Cash:       $65,558.67
Check:      $13,718.62
Credit Card: $2,690.82
            $82,287.11

Try Again

Print

Open Batch Report

| Batch | Account | Name | Type | Amount |
|---|---|---|---|---|
| 429 | | Gustafson, Jonathan (8) - Jonathan (22) - Sep 23 2003 11:11AM | | $617.98 |
| | | 2 Non-Patient Transactions | | |
| | 600-6608 | JG | Cash | $550.00 |
| | Coffee Shop | Bill Doe | Check | $300.00 |
| | | | | $250.00 |
| | | 1 Patient Transactions | | $67.98 |
| | 24549514 | Eddie Doe10067 | Cash | $67.98 |
| 428 | | Tierny, Kelly (64) - Kelly (25) - Sep 23 2003 9:52AM | | $300.00 |
| | | 3 Non-Patient Transactions | | $300.00 |
| 410 | | Anand, Ajith (31) - Station 1 (13) - Sep 10 2003 10:08AM | | $60.00 |
| | | 1 Non-Patient Transactions | | $10.00 |
| | 100-1100 | James | Cash | $10.00 |
| | | 1 Patient Transactions | | $50.00 |
| | 10109482 | James Doe-1000 | Cash | $50.00 |

Print

FIG. 15

POS System / Close Terminal

Welcome :

Terminal ID: 25

Batch Summary

If your totals do not match, please DO NOT close your batch. Press the Back button and contact Your supervisor.

[ Back ]  [ Close Batch ]

| Patient Transactions | | |
|---|---|---|
| Cash | | $2,170.00 |
| Account | | Amount |
| 10507531 | | 170.00 |
| 10507531 | | 2,000.00 |
| Check | | $3,000.00 |
| Account | Check # | Amount |
| 10807843 | 124 | 3,000.00 |

FIG. 25

Terminal Settlement (Patient Transactions)

Batch # 437
Terminal: Kelly (25)

Created On: Sep 30 2003 11:29AM    Created On: Sep 30 2003 11:57AM
Created By: Tierney, Kelly (64)     Created By: Tierney, Kelly (64)
Opening Amt: $ 100.00               Bank Bag ID: 123

Transaction Summary

| Payment Type | Transactions | Amount |
|---|---|---|
| Cash | 2 | $2,170.00 |
| Check | 1 | $3,000.00 |
| Totals | 3 | $5,170.00 |

Check List

| Check Number | Amount |
|---|---|
| 124 | $3,000.00 |
|  | Total: $3,000.00 |

FIG. 26

Release Server — Terminal ID: 0

Administration / Entities / Assign / Unassign

Entity Map: Assign / Unassign 200 licenses (100 remaining)

- [H] 1 ImageVision.net
  - + [C] 7 Harrisburg Campus
  - + [C] 8 Imagevision Test Campus
  - + [C] 10 Jasons' Test Campus
  - + [C] 12 JG Test Campus
  - + [C] 3 Kimmel Cancer Campus
  - + [C] 1 Methodist Campus
  - − [C] 5 Philadelphia Campus
    - − [D] 18 Cardio-Pulmonary 1
    - − [D] 20 ER
      - [T] 22 Jonathan Assign
    - + [D] 19 PhysicalTherapy
    - + [C] 11 Test Collection Eff Campus
  - − [C] 4 Thomas Jefferson University Campus
    - − [D] 10 ER
      - [T] 25 Kelly Unassign
    - + [D] 9 Radiology
  - + [C] 9 TJH Campus
  - + [C] 6 Torresdale Campus

Map Key
- [H] - Hospital
- [C] - Campus
- [D] - Department
- [T] - Terminal

Administration
- Settings
- Entities
  - User Accounts
  - Group Management
  - Data Imports
  - Notifications
  - Custom Reports
  - Patient Lookup
  - Transfer Categories
  - Exit

Entities
- View Entities
- Close Terminal
- Assign / Unassign
- Add / Delete / Modify

Help ?
Click on the terminal to assign it to this PC. Click "unassign" to unassign the terminal.

FIG. 34

POINT OF SERVICE TRANSACTION MANAGEMENT FOR SERVICE FACILITIES

CROSS-REFERENCE TO RELATED APPLICATIONS

This application is a continuation of U.S. patent application Ser. No. 12/763,419, filed Apr. 20, 2010, which is a continuation of U.S. patent application Ser. No. 10/719,889, filed Nov. 21, 2003, which claims the benefit of and priority to U.S. Provisional Patent Application Ser. No. 60/482,311, filed Nov. 22, 2002, and to U.S. Provisional Patent Application Ser. No. 60/428,977, filed Nov. 25, 2002, the entire disclosures of which are incorporated herein by reference as if being set forth in their entireties.

FIELD OF THE INVENTION

The present invention relates to an integrated point-of-service payment management system. In particular, the present invention provides a new, useful and non-obvious integrated point-of-service payment management solution for service facilities, such as health care facilities, thereby enabling the use of cash, credit and debit cards for collecting customer's co-payments and self-payments, and thereby enabling reporting and tracking of collection performance.

BACKGROUND OF THE INVENTION

Currently, when a customer, such as a patient, receives some form of service, such as treatment or another service, from a service provider, such as health care at a health care facility, the customer may be responsible for paying some portion of the charges associated with the service, such as treatment, such as in the form of a co-payment or self-payment. Such payments are currently accepted at the time of service with cash or check, but not generally with credit or debit card, and the remainder of the co-payments are generally billed. The acceptance of such payments only by cash or check, particularly in the health-care industry, is generally a function of a lack of integration of accounting between office locations, departments, or the like, such as a lack of integration of accounting records kept by a hospital or a doctor's office with other office systems. Further, the acceptance of such payments only by cash or check is generally a function of a lack of integration between a customer record, such as a patient record, and financial records. For example, a patient in the health care industry may visit two different departments in a hospital, within the same day, and co-payments made by that patient may not be recognized by the system as being associated with that patient in that day, or as having been payable to multiple departments in that same day, prior to departure of the patient from the hospital. Some service providers now offer an ability for customers to pay past due co-payment or self-payment balances via the internet or other after-service mechanism, but the time and effort due from the customer, in addition to the amount of the payment due, may cause many customers to not pay the past due balance.

Unfortunately, when payments due are not collected at the time payment is due, a significant amount of the revenue associated with such payments thus may be lost. This is due to the fact that, when billed co-payments cannot be collected, revenue is lost. Such non-payment of fees due increases dramatically when the customer is allowed to leave the service location without being required to make payment. Currently, individual delinquent co-payment amounts in most services industries are small —often in the range of $10.00 to $50.00—and therefore are generally not worth the cost of pursuing the customer for collection. However, such small amounts can collectively add up to millions of dollars a year.

Furthermore, even in circumstances in which balances due can be collected from customers, the cost of obtaining those past due payments may exceed the amount received from the payment. For example, major health-care providers may need entire departments staffed by large numbers of employees just to track and obtain past due payments.

Additionally, to the extent service providers, such as hospitals, do force collection of balances due upon entry or exit, limited payment locations are generally available. For example, a hospital may have only one or two locations from which payment can be accepted, and thus all customers are funneled to those one or two locations. However, the inconvenience of leaving the department the customer was serviced at, and/or the inconvenience of waiting in lengthy lines, nonetheless cause many customers to depart without making payments due.

In view of the foregoing, a need has thus been recognized for a system which allows for the collection of customer co-payments and self-pay balances through an integrated credit/debit card point-of-service system, and preferably for a system that can be implemented in various service areas within a single location, and across multiple locations (often referred to as "campuses"). The implementation of such a system would enable service providers, such as health care facilities and the like, to gain significant heretofore unrealized revenue.

BRIEF SUMMARY OF THE INVENTION

The present invention includes a method and system that enables the collection by credit/debit card payment of customer co-pay and self-pay charges via an integrated point-of-service transaction management system. The system and method of the present invention may assist health care facilities in the collection of co-pay and self-pay charges at the time service is rendered, while also providing detailed collection reporting and tracking. The present invention can be implemented anywhere cash, checks, credit cards or debit cards are accepted for payment.

DESCRIPTION OF THE SEVERAL VIEWS OF THE DRAWINGS

The various features of the present invention and its embodiments will now be described in greater detail with reference to the drawings of an embodiment of the present invention, and various related components, wherein like reference numerals designate like elements, and wherein:

FIG. 2 is a screen shot which illustrates an aspect of an embodiment of the present invention.

FIG. 3 is a screen shot which illustrates an aspect of an embodiment of the present invention.

FIG. 4 is a screen shot which illustrates an aspect of an embodiment of the present invention.

FIGS. 5A-5C are screen shots which illustrate aspects of an embodiment of the present invention.

FIG. 11 is a screen shot which illustrates an aspect of an embodiment of the present invention.

FIG. 12 is a screen shot which illustrates an aspect of an embodiment of the present invention.

FIG. 13 is a screen shot which illustrates an aspect of an embodiment of the present invention.

FIG. 14 is a screen shot which illustrates an aspect of an embodiment of the present invention.

FIG. 15 is a screen shot which illustrates an aspect of an embodiment of the present invention.

FIG. 25 is a screen shot which illustrates an aspect of an embodiment of the present invention.

FIG. 26 is a screen shot which illustrates an aspect of an embodiment of the present invention.

FIG. 34 is a screen shot illustrating an aspect of the present invention.

DETAILED DESCRIPTION OF THE INVENTION

Figure 1:
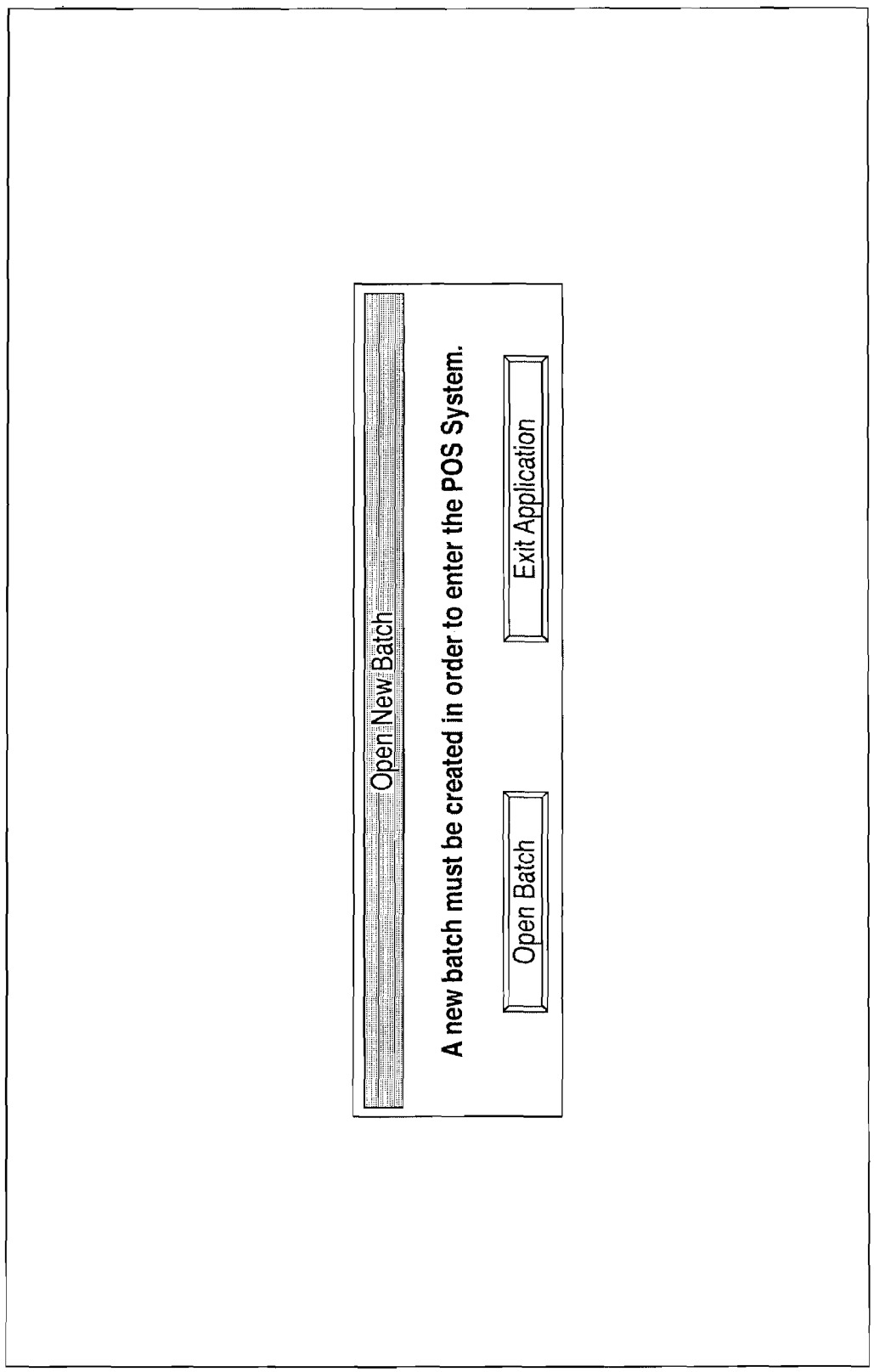
FIG. 1 is a screen shot which illustrates an aspect of an embodiment of the present invention.

It is to be understood that the figures and descriptions of the present invention have been simplified to illustrate elements that are relevant for a clear understanding of the present invention, while eliminating, for purposes of clarity, many other elements found in typical payment applications, networks and systems. Those of ordinary skill in the art will recognize that other elements are desirable and/or required in order to implement the present invention. But because such elements are well known in the art, and because they do not facilitate a better understanding of the present invention, a discussion of such elements is not provided herein. The disclosure herein is directed to all such variations and modifications to the applications, networks, and systems disclosed herein and as will be known, or apparent, to those skilled in the art.

The present invention provides for an integrated point of service transaction management system that enables the collection of fees accrued as a result of services rendered by a service provider at a single service location, or across multiple locations. To facilitate the collection of fees, a customer assessable terminal may be located at each point of service at a provider location. The terminals provide access, via a network, to at least one remote database capable of storing, accumulating and structuring information related to services associated with the customer, and capable of accessing multiple other databases. Customers may have the ability to pay or pre-pay for services, while any authorized user of the system may be able to track payments, services and the like via access to the remote database.

The present system allows for an optional and configurable "discount" in instances of immediate payment of services rendered at a point of service. Discounts or credits may also be provided for timely payments of credit accounts, overdue accounts, and the like. Discounts and credits may take the form of instant payment reduction, coupons or credits for future services, and interest-free financing, for example.

Further, the system may also provide for the standardization of cash management processes and procedures, while simultaneously providing enhanced reporting capabilities, the latter resulting in improvements in areas such as effective staff management and auditing, e.g. a "paper trail". The paper trail created allows the system to provide a tool for the auditing and tracking of transactions for every user of the system. A customer using the system may be able to track expenses and services rendered, while a provider of services may be able to audit an employee's use of time and resources, for example. System reporting may be tailored to assist a provider of services in determining profitability, efficiency and utilization, for example. Such tools are desired by both for profit and non-profit service providers, such as for the controlling of expenses and assets.

The system and method of the present invention also preferably complies with all privacy portions of federal legislation (e.g., the Health Insurance Portability and Accountability Act, or "HIPAA"). As discussed hereinbelow, user access may be provided based on varying levels of system access and information entered into the system, and thus privacy may be protected by only allowing access by authorized users with the appropriate level of access.

Importantly, the benefits of the present invention can be obtained without the investment of substantial financial resources. Due to the utilization of existing infrastructure (such as PC's, LAN/WAN, printers, servers, T-1 Internet access, etc.) and minimal hardware purchase requirements, the cost of implementing the system and method of the present invention is low. The system and method of the present invention is also capable of interfacing with existing patient management and patient accounting systems such as, for example, InVision® and Signature® (both of which are offered by Siemens Medical Solutions Health Services Corporation).

Throughout the instant disclosure, it will be appreciated that several terms may be used interchangeably with one another, some of which are discussed hereinbelow.

Referring now to FIG. 1, depicted is a screen shot to access, open, or otherwise activate a point of service (POS) terminal in the instant invention. Of note, upon log-in, or opening of the POS, the most current version of the present invention may be presented for viewing at the POS from the remote access point, thereby the present invention provides, at least in part, a thin client aspect for the use of the present invention, thus limiting processing resources needed at the POS. For example, interactions at each POS, other than those interactions discussed hereinbelow, may be entirely browser based.

The remote access point may, in an embodiment, present at the POS, upon log-in request, the most-current version of the present invention to the user as needed. As will be apparent to those skilled in the art, the presentation of the most current version at the POS may additionally entail the downloading of the most current client-side aspects of the present invention to the POS, such as aspects to run magnetic card readers, for example. Further, log-in for the present invention may be role based, wherein one or more multiple roles may be assigned uniquely to each log-in, or to each terminal-wide log-in, for example.

In FIG. 2, a new batch has been opened, such as by presentation of the latest application from the remote access point to the POS, wherein the POS may begin batching information upon opening of the POS, or wherein the POS may provide information received at the POS to the one or more remote databases in real time. It will be apparent to those skilled in the art that, thereby, information regarding all customers, in all databases, may be accessible simultaneously from any POS within the service provider at any given time, or substantially at any given time in an embodiment wherein information is batched at each POS for response to a polling application request for download to the remote access point.

As illustrated in FIG. 2, customer registration information may be requested in order to initiate a transaction. Receipt of information will cause the present invention to search existing customer databases for a match and, if no match is found, will cause the issuance of a request for information to register the customer. Upon receipt of registration of a new customer, the customer registration may be stored to the existing registration database for future accessing. If the customer information entered causes location of an existing customer or customers, matches will be returned to allow for selection of the correct customer, as illustrated in FIG. 3.

Of note, registration of a new user causes records of that user to become immediately available to all POS's through the use of the present invention. Further, it will be apparent to those skilled in the art that new customers may be registered in person at a POS, or, for example, by telephone, simply by granting registration information to a POS operator, for example.

Upon location or registration of a customer, the current transaction involving that customer may be processed for payment, as illustrated in FIG. 4. As illustrated, existing payment, or non-payment, data is integrated with current payment due data in FIG. 4, and each of the existing payment, non-payment, and current payment due data items may be resident in different databases, or at different locations, for example. As illustrated in FIG. 4, in accordance with the ability to access multiple systematic databases simultaneously, the present invention may provide prior balances due or payments made, current balances due or payments made, and the ability to pay and get approval of payment, all from a single access point. Additionally, certain balances may be flagged, such as by color, in instances wherein those balances are of particular note, such as wherein the flagged balances constitute "bad debt" that has been unpaid for greater than a specified time. For ease of use, a "mouse-over" feature may be made available, whereby a user may place the cursor over payments paid or due in the payment screen, and may be shown predetermined relevant information regarding the payment correspondent to the cursor location.

Upon entry of a payment, for example, the system may track the type of payment, go outside the system via the network to gain any necessary payment approvals, such as credit card approvals, and pay down balances with that payment, such as in a cascade format wherein the current amount due, and then each subsequent oldest balance due, in turn, are paid, from the access screen of FIG. 4. As illustrated, typical payment options may be accepted at the POS, including, but not limited to, cash, credit cards, debit cards, and EFTs, for example.

As illustrated in FIGS. 5A, 5B, and 5C, selection of different payment methodologies may present different information requests to the user of the POS, wherein the user may be a customer or a facilitator. Alternatively, upon swiping of a payment card in a card-reader associated with the POS, like information regarding the customer purchase method may be generated automatically. Further, as illustrated, the payment screen may include relevant payment codes, each of which may correspond to areas within, or associated with, the service provider location. Thereby, only certain eligible payment codes may be accepted for current payments due in the screens of FIG. 4 and FIGS. 5A-5C.

The inclusion of payment codes allows for acceptance at a POS of payments from multiple categories of an accounting ledger. For example, in a health care facility, payments may be accepted for patient services, and non-patient services, differentiable by entry of the relevant accounting code for the services provided, in conjunction with the receipt of payment, at the POS. Thereby, an audit trail is created through the use of the present invention, at least in that the required accounting code may be associated with any received payment, and may additionally be associated with the location and terminal identification at which the payment was received, and the user logged to that terminal at the time of payment. Thus, receipts printed in hard form, as discussed hereinbelow, may provide a paper audit trail, and tracking via the one or more remote databases may provide a soft copy audit trail.

Figure 6:
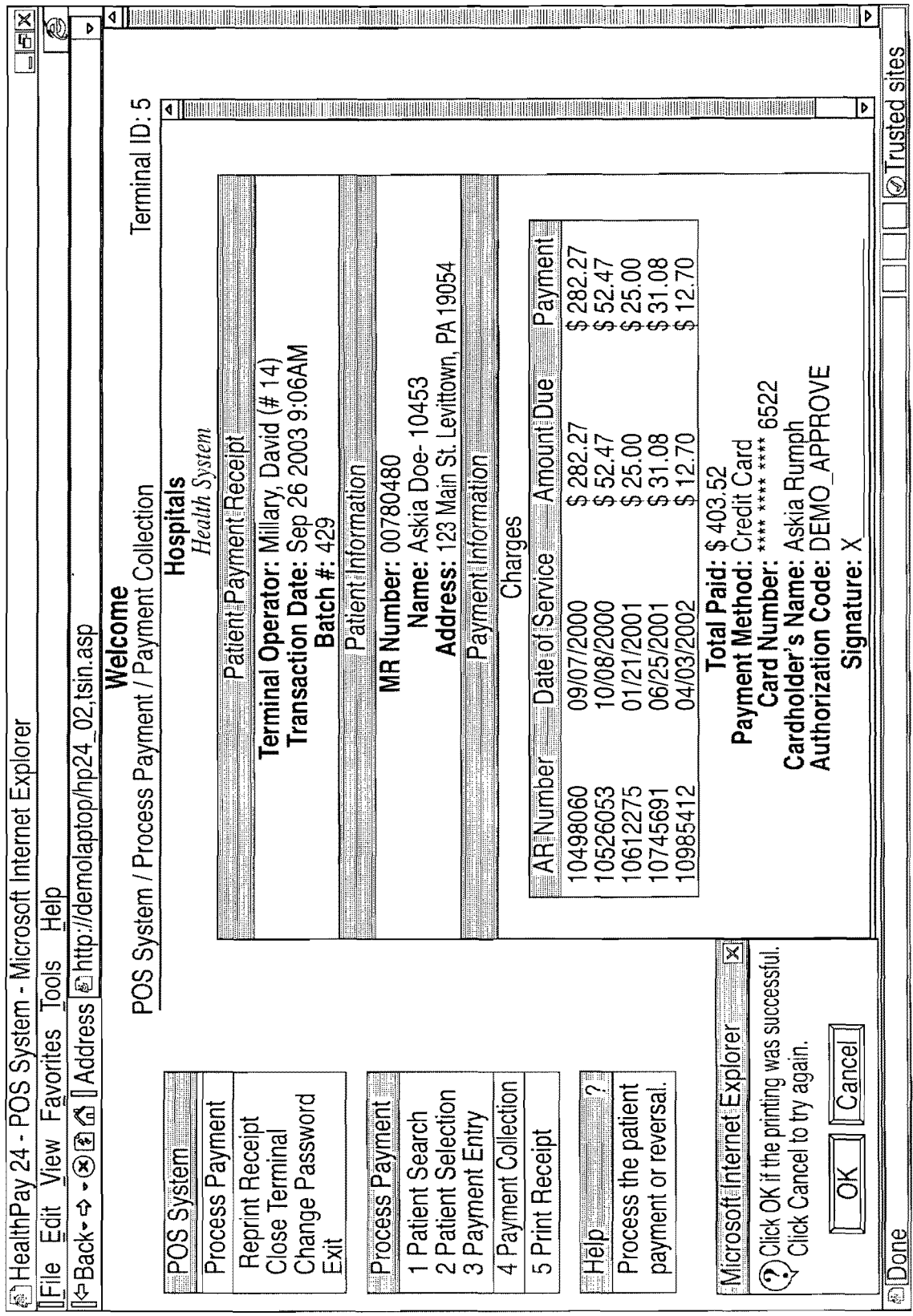
FIG. 6 is a screen shot which illustrates an aspect of an embodiment of the present invention.

Upon receipt and approval of payment, a receipt may be generated, such as that shown in FIG. 6. The receipt may be generated in soft-form, and may be stored to one or more databases in the system of the present invention, and may be printed in hard-form and given to the customer, as well as being stored in hard-copy files at the service provider location. Hard copy receipts may be generated by request at the POS, or automatically.

Figure 7:
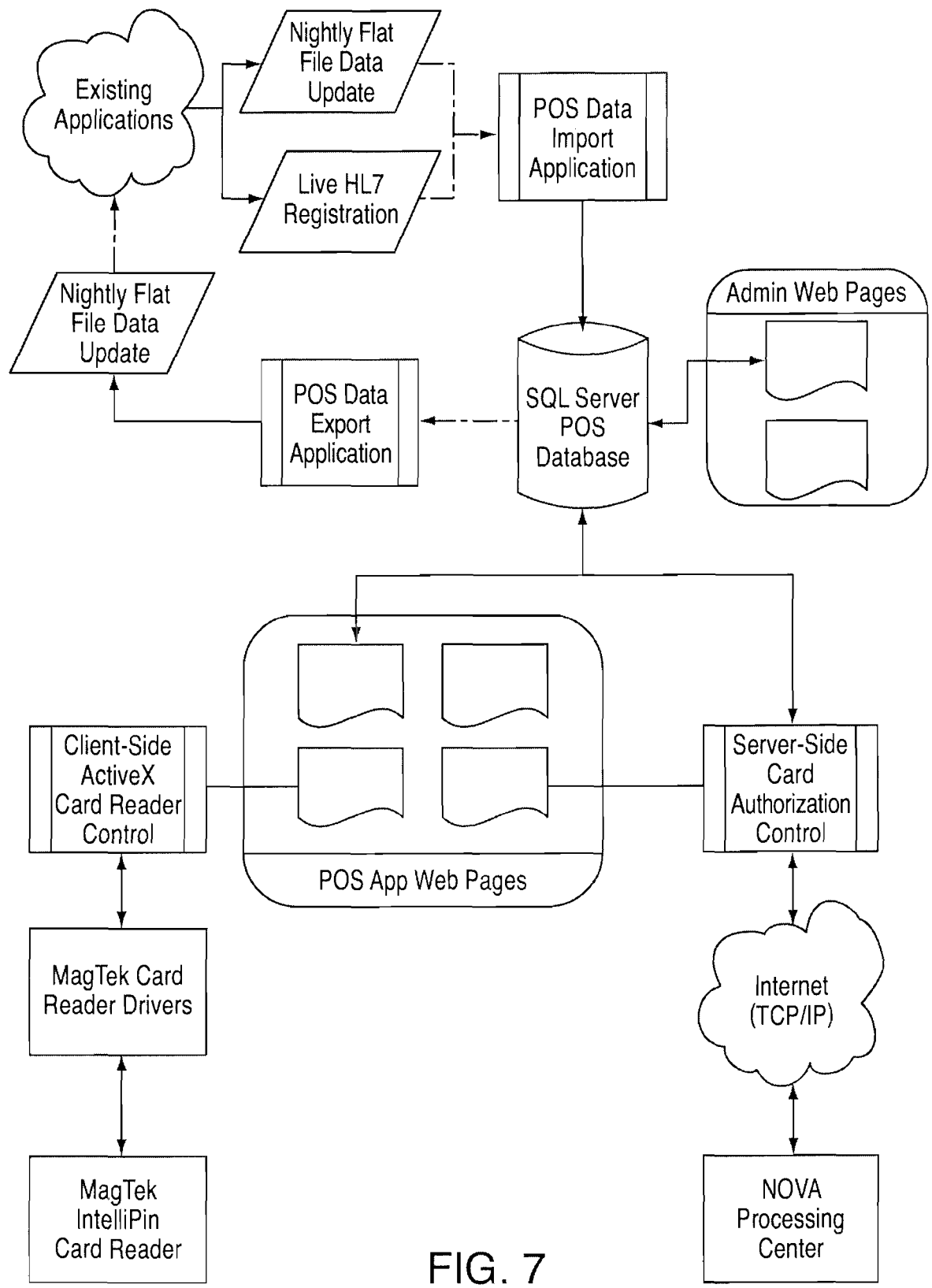
FIG. 7 is a block diagram which illustrates the general architecture of an embodiment of the present invention.

Referring now to FIG. 7, depicted schematically is a visual representation of a payment system in accordance with the present invention discussed in the screen flow hereinabove. Various aspects of the system shown in FIG. 7 will be further appreciated from the discussion of the figures provided further hereinbelow.

With respect to the discussion of the Figures hereinthroughout, and as used herein, HTML, or HyperText Markup Language, refers to one of the authoring languages used to create documents on the World Wide Web. HTML, as used herein, is contemplated as exemplary of network programming languages, and is thus interchangeable with other terms and programming language types that will be apparent to those skilled in the art, including, but not limited to, Java, XML, XSL, xHTML, and the like. HyperText Transfer Protocol (HTTP), and associated protocols with other language types, are the underlying protocols used by the World Wide Web. HTTP and similar protocols define how messages are formatted and transmitted, and what actions Web servers and browsers should take in response to various commands. For example, when a URL is entered into a browser, this sends an HTTP command to the Web server directing it to retrieve and transmit the requested Web page.

As used herein, a link or hyperlink is a navigational link from one document to another, or from one portion (or component) of a document to another. Typically, a hyperlink is displayed as a highlighted word or phrase that can be clicked on using the mouse to jump to the associated document or document portion.

As used herein, a network, such as an internet, intranet, or extranet, is a collection of interconnected public and/or private computers or computer networks that are linked together by a set of standard protocols, such as TCP/IP, HTTP, FTP and Gopher. A network may be or include: a LAN (local area network), which is a computer network spanning a relatively small area, but which may be connected to other LANs to form larger networks, such as by telephone lines, leased lines, satellite, radio communications, or a T-1 line; or a WAN (wide area network), which is a network spanning a larger area, and which may be formed of interconnected ones of the LANs. In a typical embodiment, a LAN may connect a series of workstations and PCs to at least one server, and one or more nodes on a LAN may include a CPU that executes programs and/or platforms.

The system and method of the present invention, as illustrated with respect to FIG. 7, may include a browser-based point-of-sale system running over an existing LAN/WAN that is easy to maintain and support, such as a web browser interface running in association with at least one MS SQL Server 2000 and at least one Web page server, and that may be integrated with one or more legacy systems. Devices utilizing wireless LAN, i.e. WI-FI, may be connected to the present invention. Co-payments or self payments may be collected at various service areas throughout one or more facilities, such as by using existing PC's as point-of-service terminals. Acceptable forms of payment may include, but not be limited to, cash, checks, credit cards (e.g., Visa®, MasterCard®, American Express®, Discover®) and debit cards, such as with the use of a personal identification number (PIN).

Specifically, as illustrated in FIG. 7, the system and method of the present invention may make use of manual cash amount entry and magnetic card swipes and/or PIN pads at each point-of-service (POS) terminal whereat services are offered, thereby providing for fast and reliable credit/debit card processing. In an embodiment, credit card and debit card transactions may be processed over the Internet rather than over analog lines, thereby significantly reducing costs and providing for a quick response time for credit/debit transaction approvals (i.e. under 10 seconds per transaction).

As illustrated in FIG. 7, customer data may be taken upon customer registration at the POS. Alternatively, the customer registration may be integrated with prior registration from existing systems, which systems may provide an ability to recognize the existing customer, to associate payments made with that customer, and/or to pull records of that customer, among other actions, simply based upon entry of a customer data item, such as a name, phone number, or swipe of the customer's card for payment, to the system of the present invention. For example, a patient may be seen in Dept. A of a hospital, and the doctor in Dept. A may electronically pull that patient's chart and payment records, make a diagnosis, electronically enter that diagnosis, such as in a "notes" section of the input, and have entered for that patient a current payment due. The patient may then proceed to the exit of Dept. A, at which point the patient may be checked for registration, may present an amount currently due, may swipe a credit card to allow for collection of a co-payment currently due for the treatment received in accordance with the current payment due previously entered. Additionally, prior balances due may be paid by the customer. The card reader, for example, may, via the internet, request acceptance of the payment, and may return an acceptance of the entered current payment, and/or payment of one or more prior balances. The system of the present invention may then access that patient's records, the treatment received, any past-due balances, and the current diagnosis including any prescription reminders, from the legacy systems of Dept. A, and may adjust such data as necessary in light of the transaction.

More specifically, with respect to FIG. 7, a series of existing legacy applications, and the system of the present invention, may receive and/or provide accessibility to a plurality of updated flat files, which may be updated in real time, such as through the use of the present invention, and such as at the POS, and/or which may be batch updated, such as nightly. The data to update these existing applications may be exported from the POS application, via the use of the present invention, and the data from these flat files may be imported to, or exported from, the POS, via the existing applications or via other POSs of the present invention, such as via real time access, or via a polling of the applications, for example. Access via a network to internal and external applications may thus be provided via the use of the present invention, such as via an SQL server. Such SQL server may thereby interconnect and/or interact with both a centralized administrator and the POS.

Figure 8:
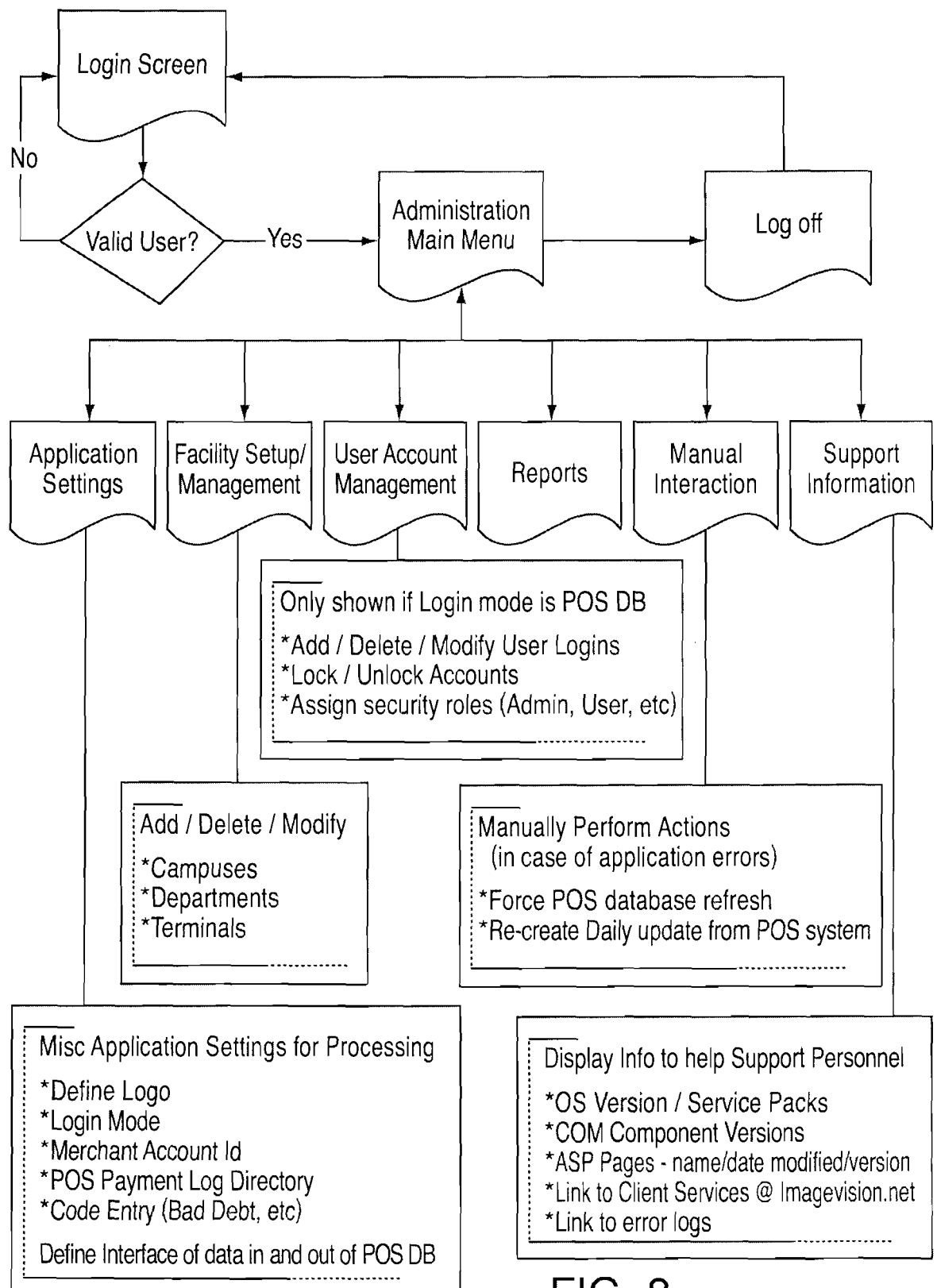
FIG. 8 is a block diagram depicting an administrative overview of the system of the present invention.

FIG. 8 illustrates an embodiment of an administrator for use in the present invention. The administrator may be, in whole or in part, resident at a centralized location communicatively connected to each POS at the service provider, and/or may be resident, at least in part, at each POS. The administrator may allow for logging of registered users, such as by entry of a user name and password, and may provide levels of access by user or permission type, in accordance with the user or permission type associated with the particular login entered, which association may be provided, for example, in at least one database within, or associated with, the administrator.

For example, the system and method of the present invention may include three levels of user security, such as POS User, POS Supervisor, and POS Administrator. The POS User may have the lowest level of access to the system. The POS User can thus log into a POS terminal, collect payments, and close out a POS terminal. The POS User can change a password but cannot perform other supervisor or administrative tasks. The POS Supervisor may have the same privileges as the POS User but may also perform additional activities, such as re-assigning default printers to POS terminals, maintaining user profiles for a department, closing out a department, and reporting. There may typically be one POS Supervisor per service area or department. The POS Administrator may have the same access privileges as the POS Supervisor but may also perform additional activities, such as setting up POS Supervisor user profiles, defining and modifying the topology (Campuses, Departments, POS Terminals, Network Printers), and all reporting.

Within the administrator, a main menu page, which may be selectable and navigable via methods apparent to those skilled in the art, such as pull-down menus, hot keys, treed menus, links, hyperlinks, and the like, may provide access to settings, setup, account management, generating reports, manual overrides, and support/help, for example. Settings may provide the manner in which the application process progresses, such as whether current payment is enabled when there is an existing debt, flat file update recurrences, and the like. Setup may allow for setup for certain facilities, such as adding, deleting, or modifying campuses, departments, groups, offices, terminals, and the like. Account management may allow for master control of accounts, such as numbers of accounts, user permissions and security roles, and the like. Administration may additionally provide, for example, maximum open times for each POS, accounting codes allowed, discounts, HL7 and flat file interface settings, allowable payment types, one or more entity trees defining all related entities, and relevant locations, in a service provision system, and the like.

Figure 35:
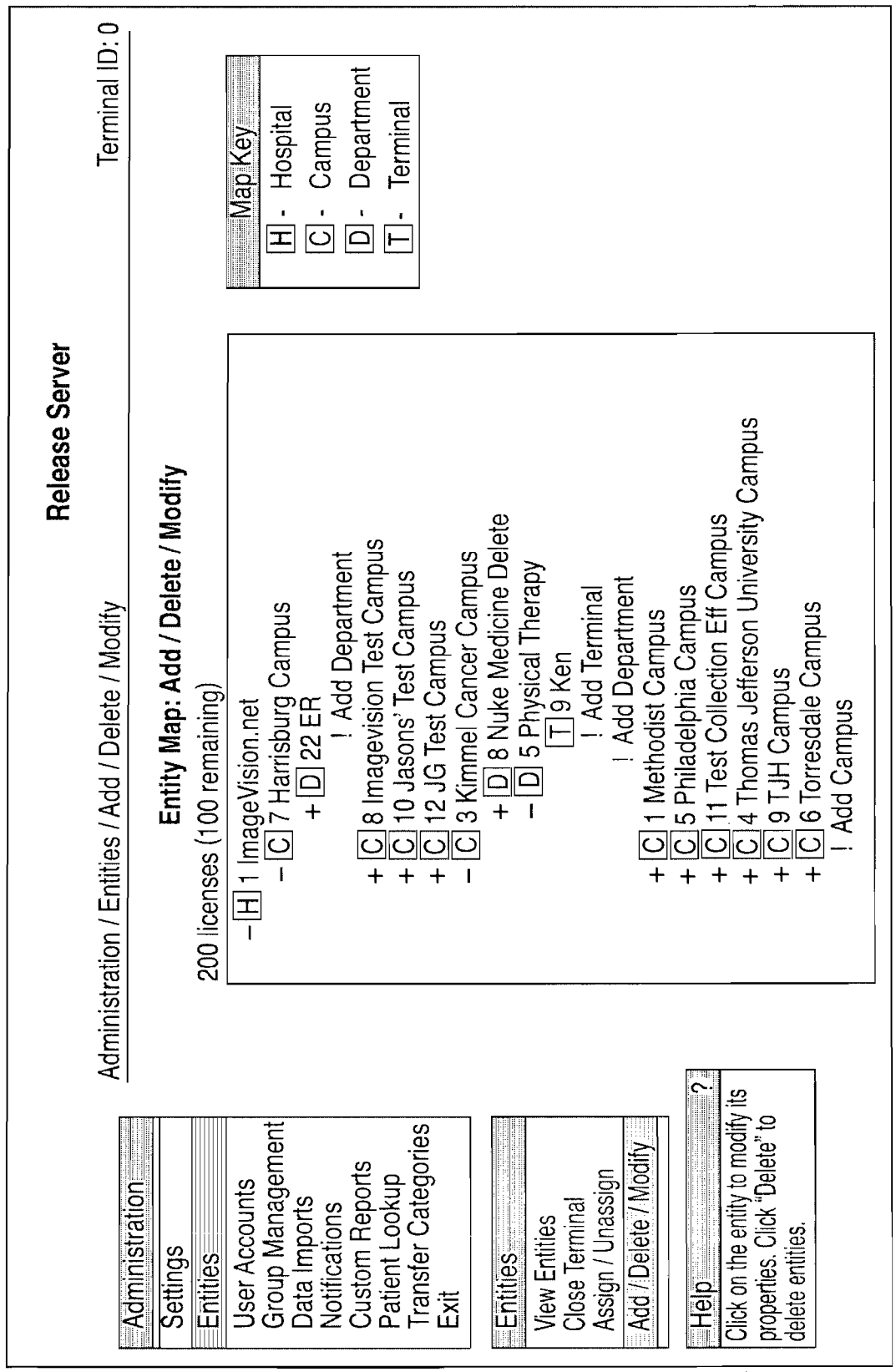
FIG. 35 is a screen shot illustrating an aspect of the present invention.

For example, to facilitate administration, an entity tree may be available via one or more POS's for an authorized accessor, and may thereby map locations, campuses, departments, and all POSs in any service provision system, keyed by level of each POS. Such an entity map may be available via a single viewing screen, for example. Further, for example, FIGS. 34 and 35 illustrate an embodiment of such an entity map, and the manner in which such an entity map may have made thereto additions, deletions, and/or modifications. As illustrated in FIG. 34, a service provider may be hierarchically organized by system, hospital, campus, department, and actual terminal at the POS. The treed entity map may be expanded or retracted, such as by selecting plus or minus buttons adjacent to the relevant portion of the tree. As illustrated in FIG. 35, hospitals, campuses, departments, or terminals may additionally be added or deleted or modified, such as with a convenient click, as necessary or desired, through the use of the present invention. This may additionally allow for reporting at each level in any system, as discussed further hereinbelow.

Reporting may allow for generation of administrative reports, and may be accessible from within the administrator or from each POS. For example, the present invention may provide for generation of end-of-shift and batch or department closure reports, as well as pre-defined payment transaction reports, and additionally may log errors, notes on each transaction, such as for batch delivery to back-end accounting, or the like. Further, for example, the present invention may provide, via the administrator main menu or the POS, the production of user-defined payment transaction reports using third party software, such as Crystal Reports® (Seagate Software, Inc.). Manual interaction and override may allow for manual control of generally automated processes, such as forcing actions to be taken.

Figure 9:
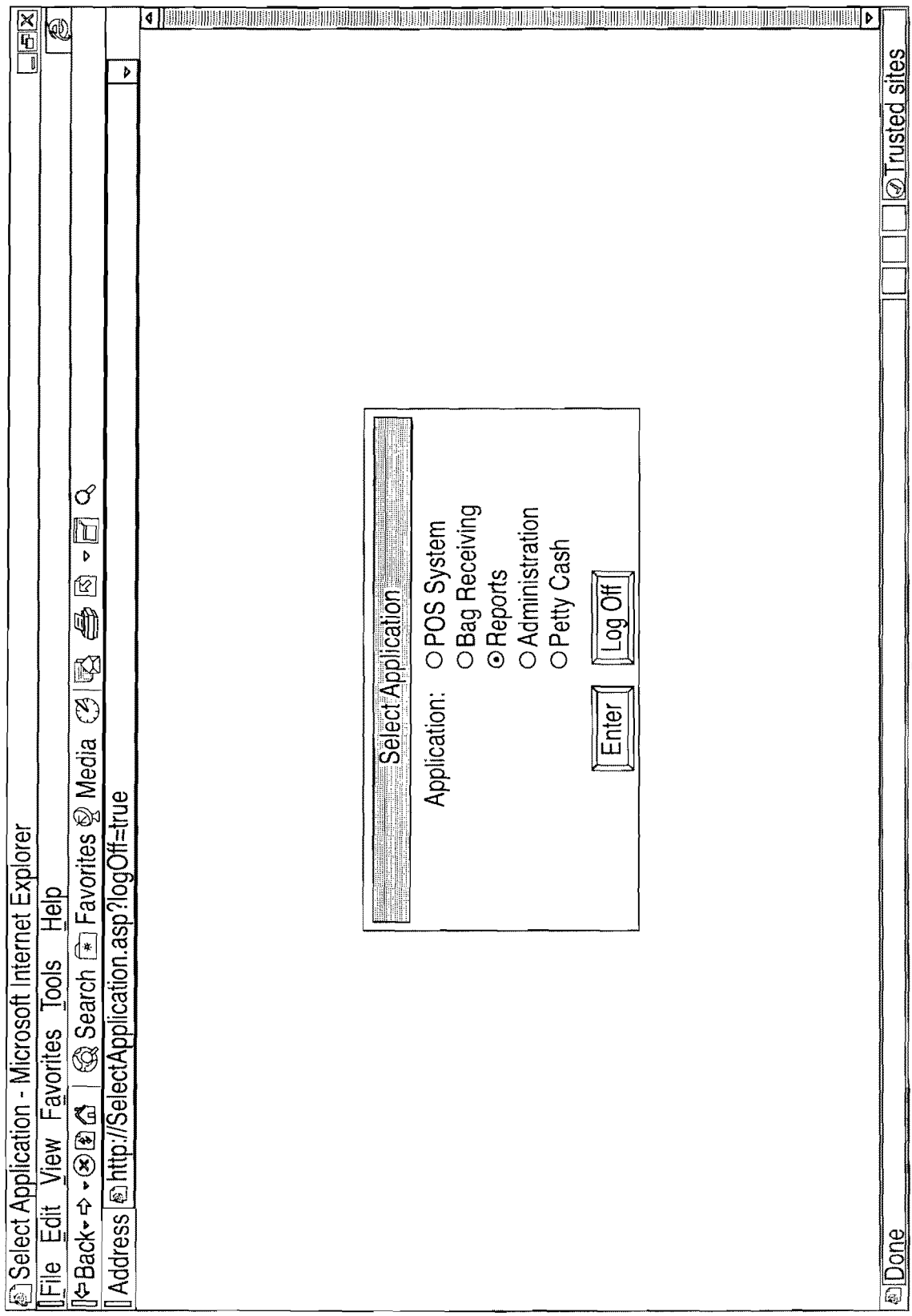
FIG. 9 is a screen shot which illustrates an aspect of an embodiment of the present invention.
Figure 10:
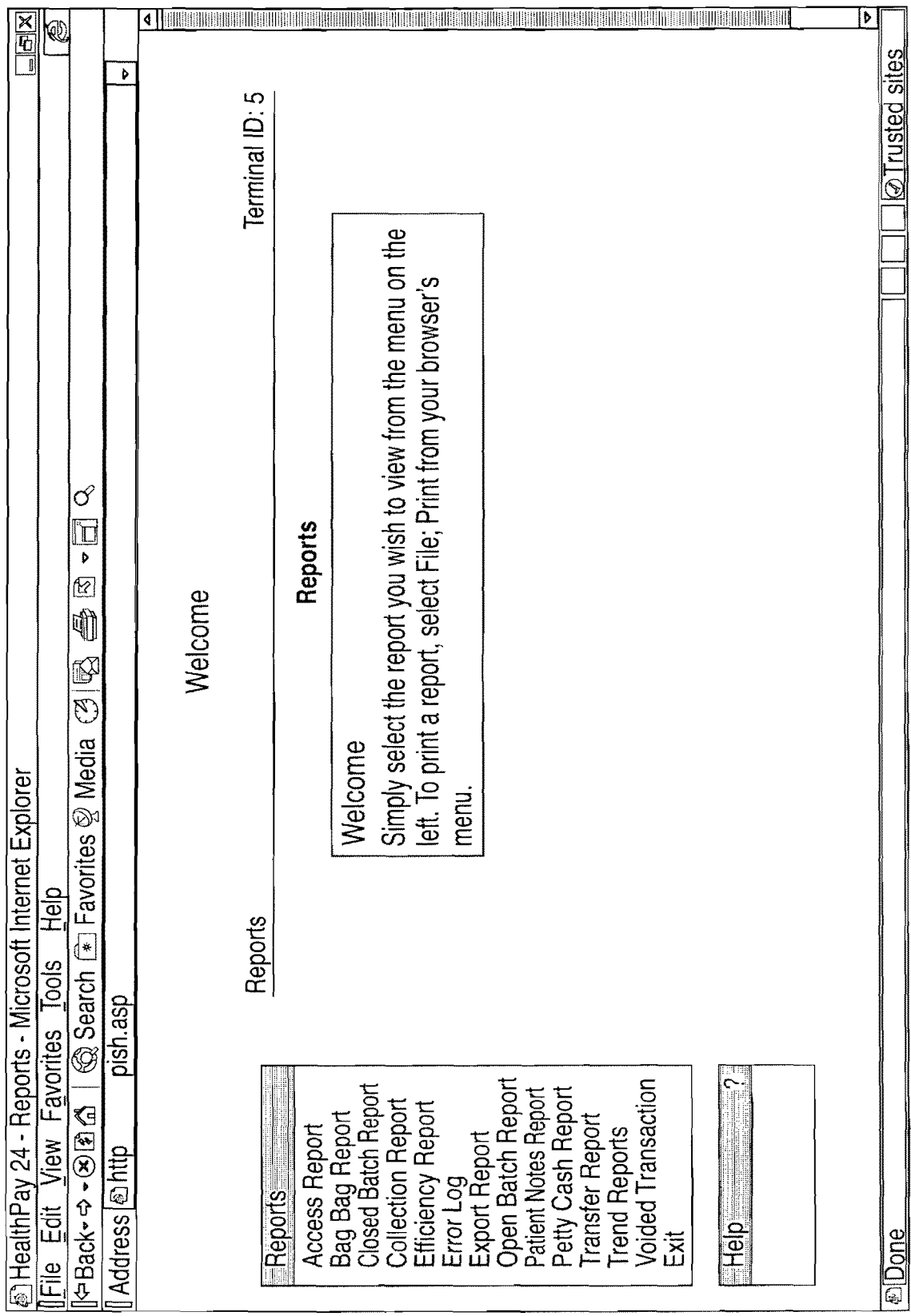
FIG. 10 is a screen shot which illustrates an aspect of an embodiment of the present invention.

Reports may be accessed, from the administrator and/or from the POS, by selecting a "Reports" selector as illustrated in FIG. 9. Available reports may be selectable from a menu, such as a treed menu or split screen menu, as illustrated in FIG. 10. Reports may allow for a review of, for example, terminal operator efficiencies, terminal efficiencies, terminal transactions, or the like, as illustrated in FIGS. 11 and 12. Such reports may additionally be available by provider site, for overall terminals present at each site, such as the report illustrated in FIG. 13. Reports may preferably be available upon the closing of one or more terminals, and thereby upon generation of a batch update from those one or more terminals, for example.

Figure 14:
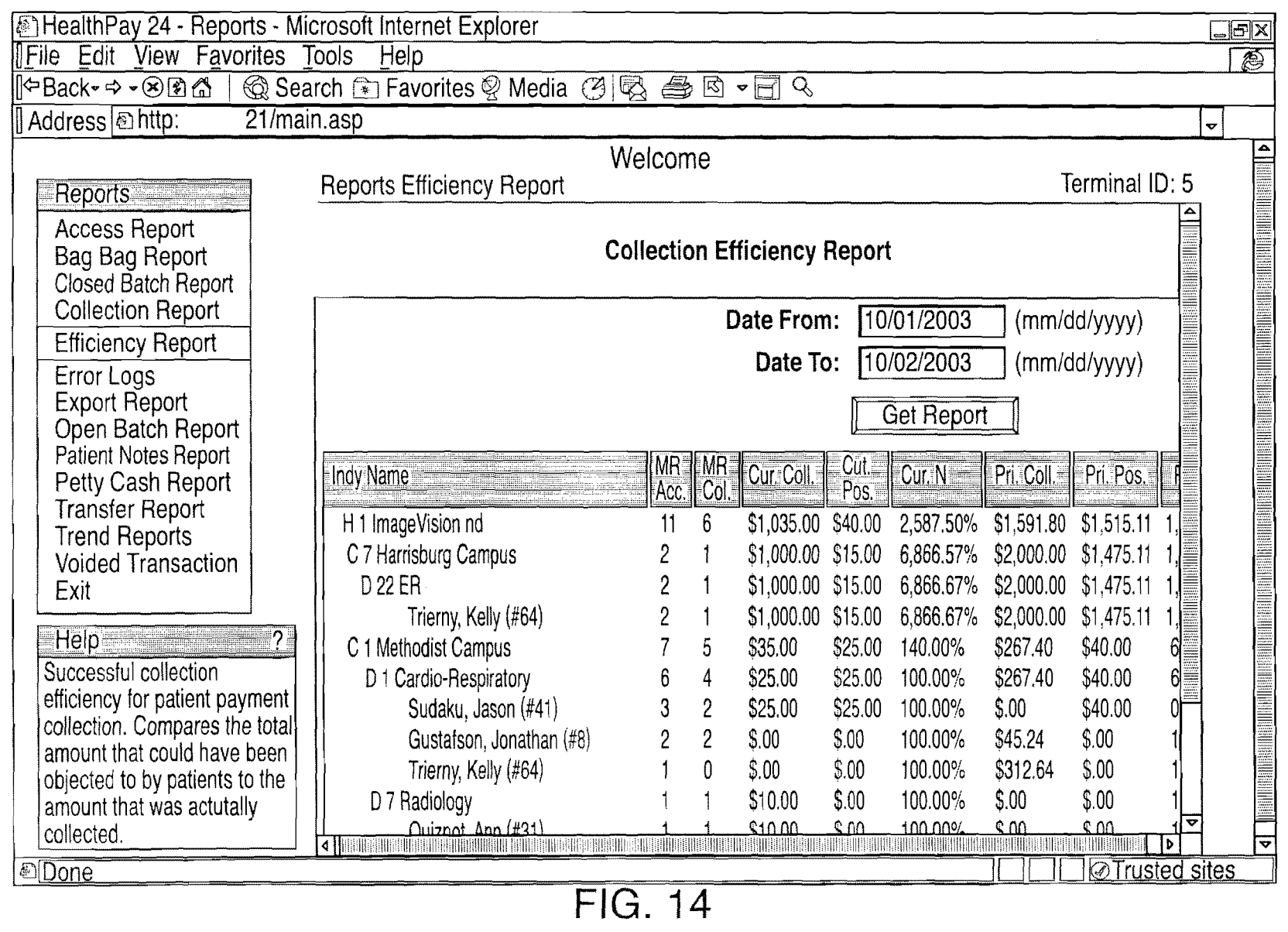

In a specific reporting embodiment, the use of the system and method of the present invention across a service provider location or locations may allow for generation of efficiency reports, such as that illustrated in FIG. 14. As illustrated, the present invention may track registered collectibles versus attempted collections, patients registered versus patients collected from, amount collected versus amount that could have been collected, and like factors reflecting the efficiency of collections for a service provider per terminal or per site.

In an additional exemplary reporting embodiment, an open batch report may be generated, as illustrated in FIG. 15, whereby open batches, i.e. active terminals, are reported. Such a reporting may include both open and closed batches, and may provide the time for which batches have been open. For example, to the extent particular batches have been open, or have otherwise gone un-reconciled, for greater than a predetermined time frame, those batches may be flagged in the report, such as being illustrated in red color.

Returning now to FIG. 7, the POS may include a series of links, hyperlinks, and/or web pages that provide access to and interconnect at least one network with accessibility to credit and/or debit card authorization applications, and that provide access to a plurality of card readers that provide for the swiping or typing of card information, for entry of that information as discussed hereinabove. In an exemplary embodiment, MagTek® IntelliPIN® magnetic stripe readers and PIN entry pads, by MagTek, Inc., may be employed in conjunction with one or more Web server/payment servers and an Internet connection, such as a T-1 or higher connection, to effectuate the reading and approval of debit and/or credit cards. In a preferred embodiment, a device such as the MagTek® IntelliPIN® may combine a magnetic stripe card reader and PIN entry pad, may be secure and tamperproof, may encrypt data, such as user PIN numbers, automatically for added security, may be small enough to conserve space, may provide graphical interface for a customer-user to easily engage the unit without training, and may be easily attached to a PC designated to be a POS terminal. An exemplary flow of this POS aspect of the application of the present invention is illustrated with more particularity in FIG. 16.

The real time accessing of payment data securely allows for the up-front payment of co-payments and self-payments, for example. Such up-front payments eliminate bad and uncollectable debt, and thereby provide an improvement over the back-ended payment systems of the prior art. Further, in an embodiment wherein information, such as payments, is tracked in real time, knowledge of payments as those payments occur is an improved methodology of eliminating bad debt over the occasional updates of the prior art. Also, back-end payments remove incentives on the customer to pay, as services have already been received and the customer has left the premises in back-end payment systems. For example, a customer is inconvenienced in systems wherein the customer, after departing the location of the service provider, is to access a payment site via the internet, and the customer, after having departed, has no incentive to suffer that inconvenience. Up-front payment eliminates this disadvantage. Further, up-front payment allows for elimination of the expense of bill generation, delivery, and processing after a customer visit. Additionally, up-front payment may eliminate customer confusion over bills received months after services are provided. Thus, as will be apparent to those skilled in the art, up-front payments and elimination of bad debt provide for increased revenue for the provider of the method and system of the present invention.

Figure 16:
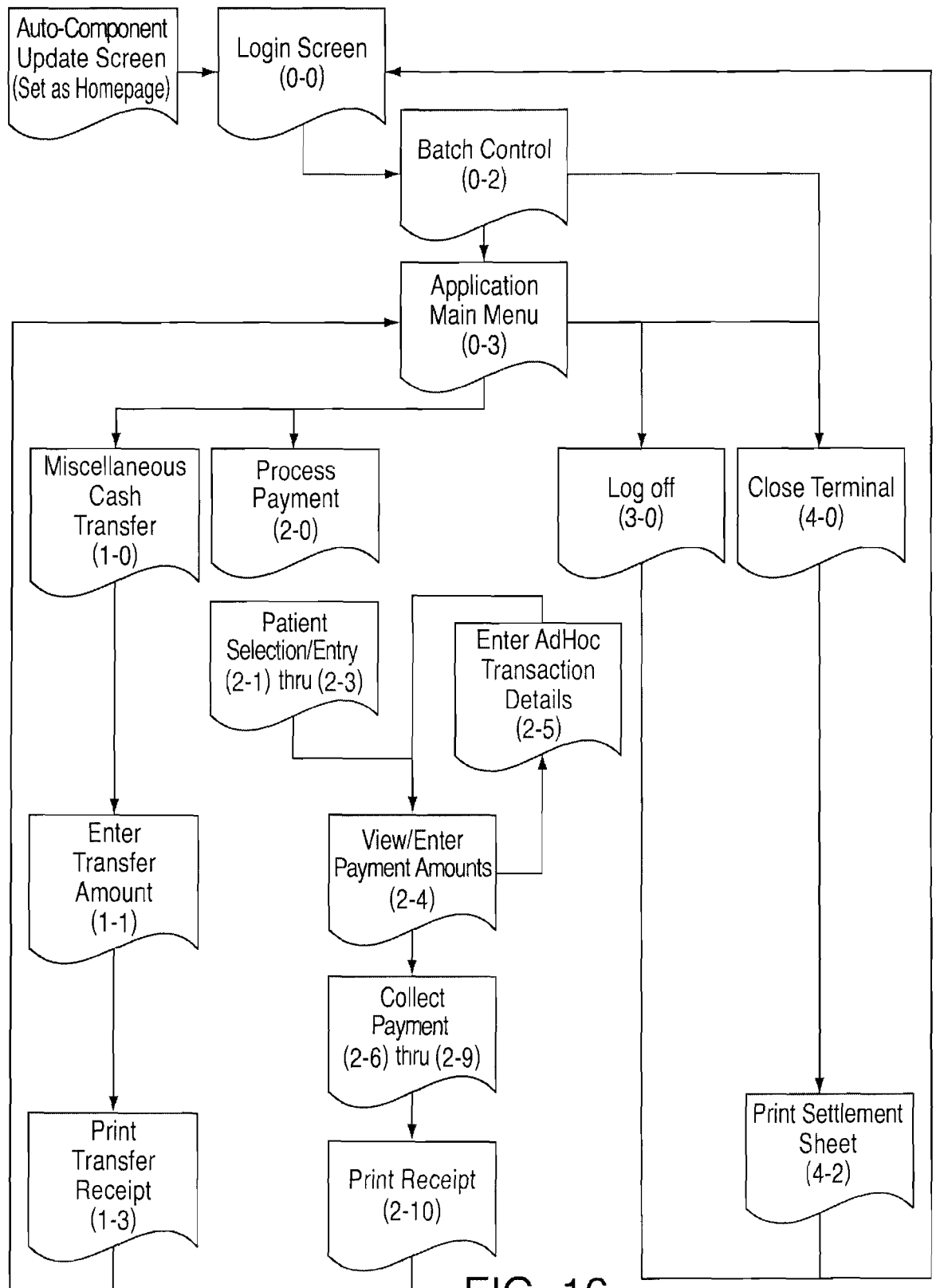
FIG. 16 is a block diagram depicting an overview of the Point-of-Service Application of the system.

As illustrated in FIG. 16, a customer or facilitator may have access to, for example, a card swiper or keypad entry, or additionally to, an interactive screen, such as a touch screen, to allow for interaction with, and entry of card information to, the POS. Further, a facilitator, such as a cashier, may have access to the POS information available regarding the customer, and/or to additional information not within view or access of the customer, as discussed hereinabove. The application main menu at the POS may allow for entry of card information, or entry of cash payment, or entry of a cash transfer, such as an EFT, for approval from a remote authorizer, as discussed hereinabove, which approval may be accessed, for example, via a network, also as discussed hereinabove.

Thereby, such swiped card authorization, or past due balance information to be paid by the swiped card, may be associated with payment information from other groups, offices, or departments of the same entity, or within the same facility, such as via the batch updates upon terminal closure for that POS. For example, a patient balance due from an X-ray in a medical center may be added with a balance due from a gift shop and from a cafeteria to generate a total balance due.

Further, as illustrated hereinabove, swiping or entry of a card or patient name or information may cause the accessing of customer, such as patient, records, including viewing and entering payment amounts, which may include past due payments, entry of transaction details, and/or generation of a receipt. Thus, the system and method of the present invention may provide for an audit trail by quick receipt printing using existing network printers, such as printing two copies of the receipt on plain white 81A×11 paper, for example. Further, the POS may provide for batch control, such as generation of batch updates from that POS to the flat file updates.

Figure 17:
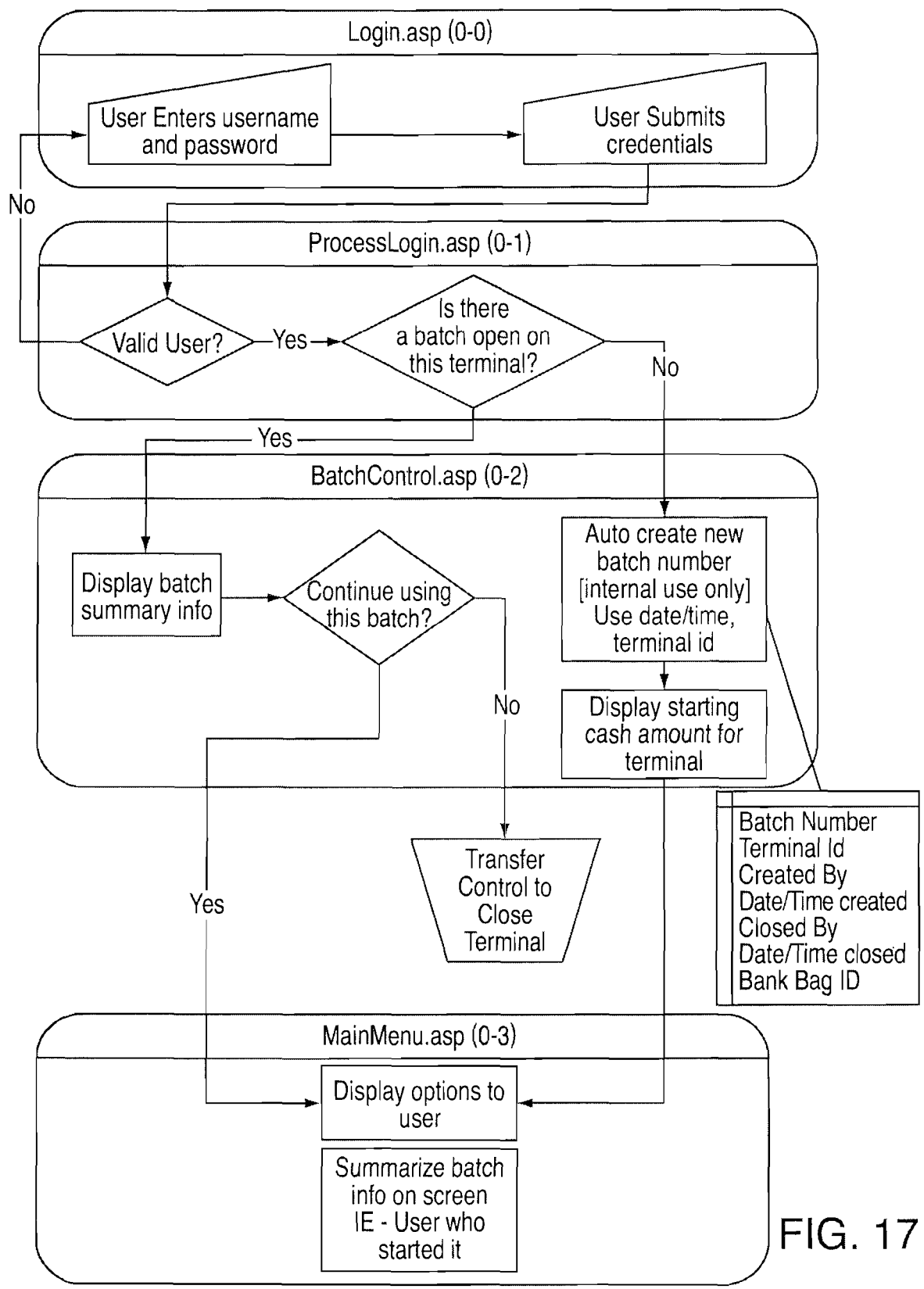
FIG. 17 is a block diagram which illustrates the operation of the Main Menu of the system.

Batch interface files may be produced to update current customer, such as patient, accounting systems with payment or other information. Further, the present invention allows patient registration information to be accepted real-time in HL-7 format (an ASTM-defined common communication format for healthcare electronic data transfer) from existing patient management systems, and allows for batch association of that registration information with other information, such as payments due. FIG. 17 illustrates the flow of a batch control performed at, or in association with, the POS of the present invention.

Figure 18:
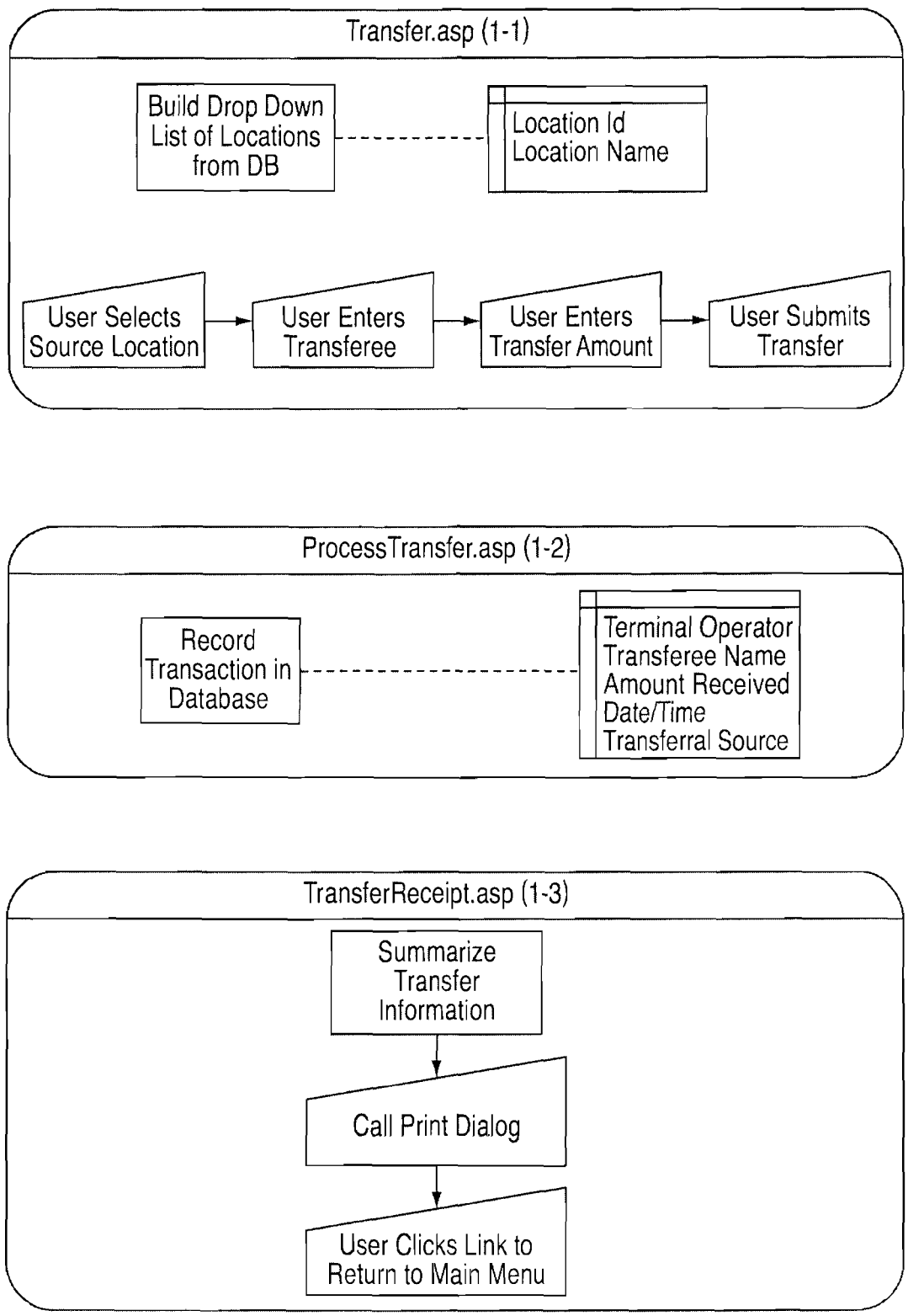
FIG. 18 is a block diagram which illustrates the operation of the Cash Transfer function of the system.

As illustrated in FIG. 17, a user may login and have the necessary permissions to engage the batch processes. An authorized user may engage in batch control, such as by viewing batch information, creating new batches or using the current batch, viewing the cash or dollar value of the current batch, and the like. FIG. 18 further illustrates recordation of a transaction, in a specific embodiment implementing a value transferal.

Figure 19:
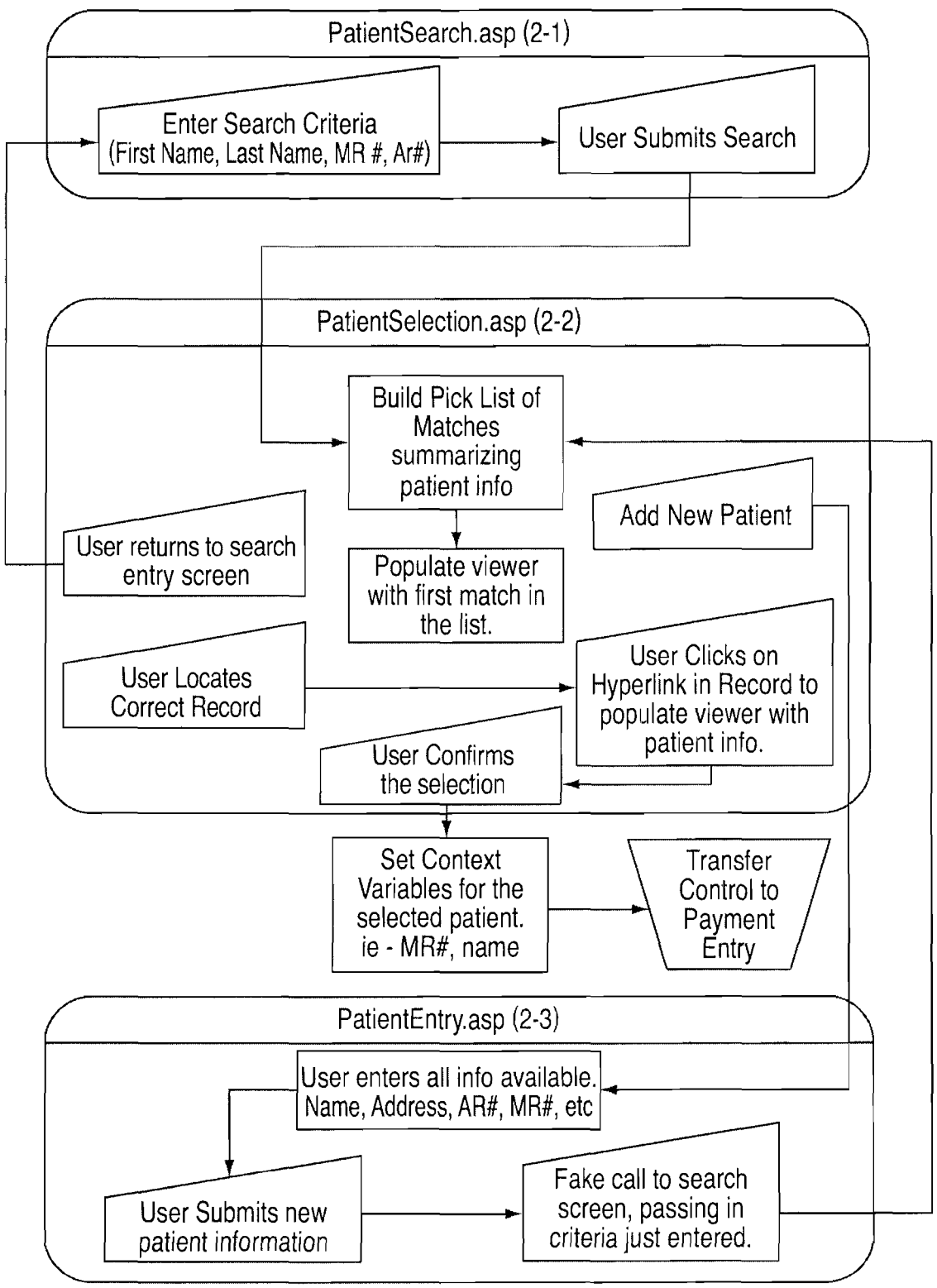
FIG. 19 is a block diagram which illustrates the operation of the Process Payment function of the system.

FIG. 19 illustrates an implementation of the system and method of the present invention wherein a particular customer, such as a patient, may be searched for and/or selected. For example, a POS user may enter a search criteria, such as via a POS terminal, to locate a particular customer. That search may activate both the POS and legacy systems, may access the files thereof, and may return a listing of customers matching the search criteria, as discussed hereinabove. If no matches are returned, the customer may be added as a new customer, such as via the POS. If one or more matches are found, the customer record may be accessed, such as via a hyperlink to the location of the matching records, and all fields of the terminal may be populated by the selected matching record.

In an exemplary embodiment, the search for a matching customer may be performed on all records, including legacy records, via a translation of all records to a format acceptable to the system of the present invention, including such as by a batch download of converted legacy files accumulated at intervals. For example, a set of data types for existing legacy systems may be entered to the system of the present invention, and, upon an activation of accessing legacy records, the system and method of the present invention may endeavor to match the legacy records at the to-be-searched locations to one of the known data file types. Once a matching type is found, the records may be accessed and translated to a format suitable for use in the present invention.

Figure 20:
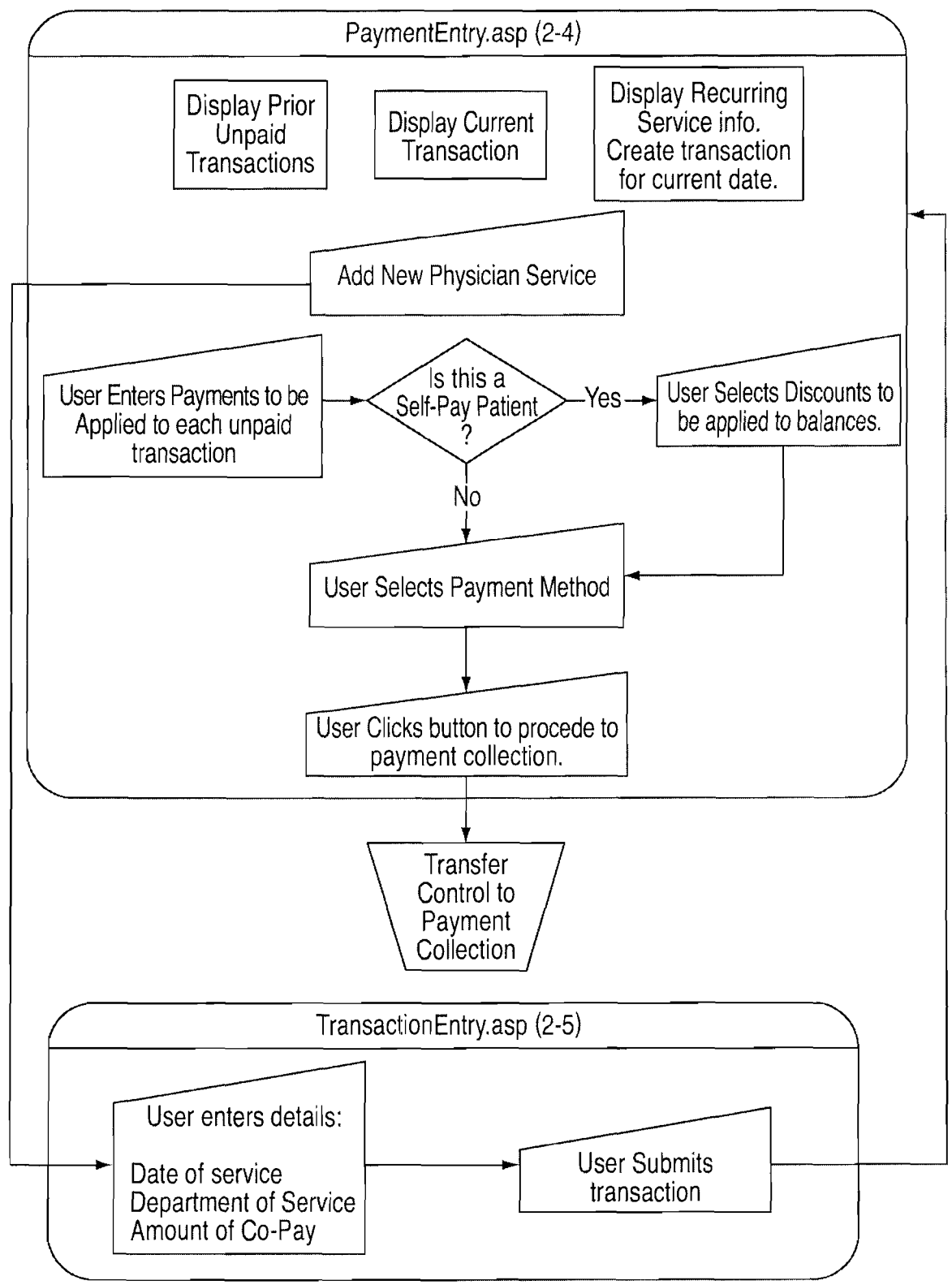
FIG. 20 is a block diagram which illustrates the operation of the Payment Entry function of the system.

FIG. 20 is a flow diagram illustrating the entry of payments and transactions to the POS. For payments, the POS display may display, to the customer and/or the facilitator, the current payment due, related and recurring payment information, and any overdue balances for any departments. The customer may self pay, or co-pay, via payment entry, and may select the payment method and any discounts, coupons, or the like to be applied, as illustrated hereinabove. The facilitator may enter the transaction occurring at the POS, such as into a transaction entry interface, which entered transaction may include details of the transaction, such as payments due, services rendered, and the like.

The transaction so entered may additionally include the entry of transaction notes. Such notes may provide a communication channel between front-ended personnel, such as those at the POS, and back-ended personnel, such as those in accounting. For example, such notes might include that a past due balance was not collected because the customer asserted at the POS that a check had been sent the previous day, and such a note may thereby alert accounting to that fact.

Figure 21:
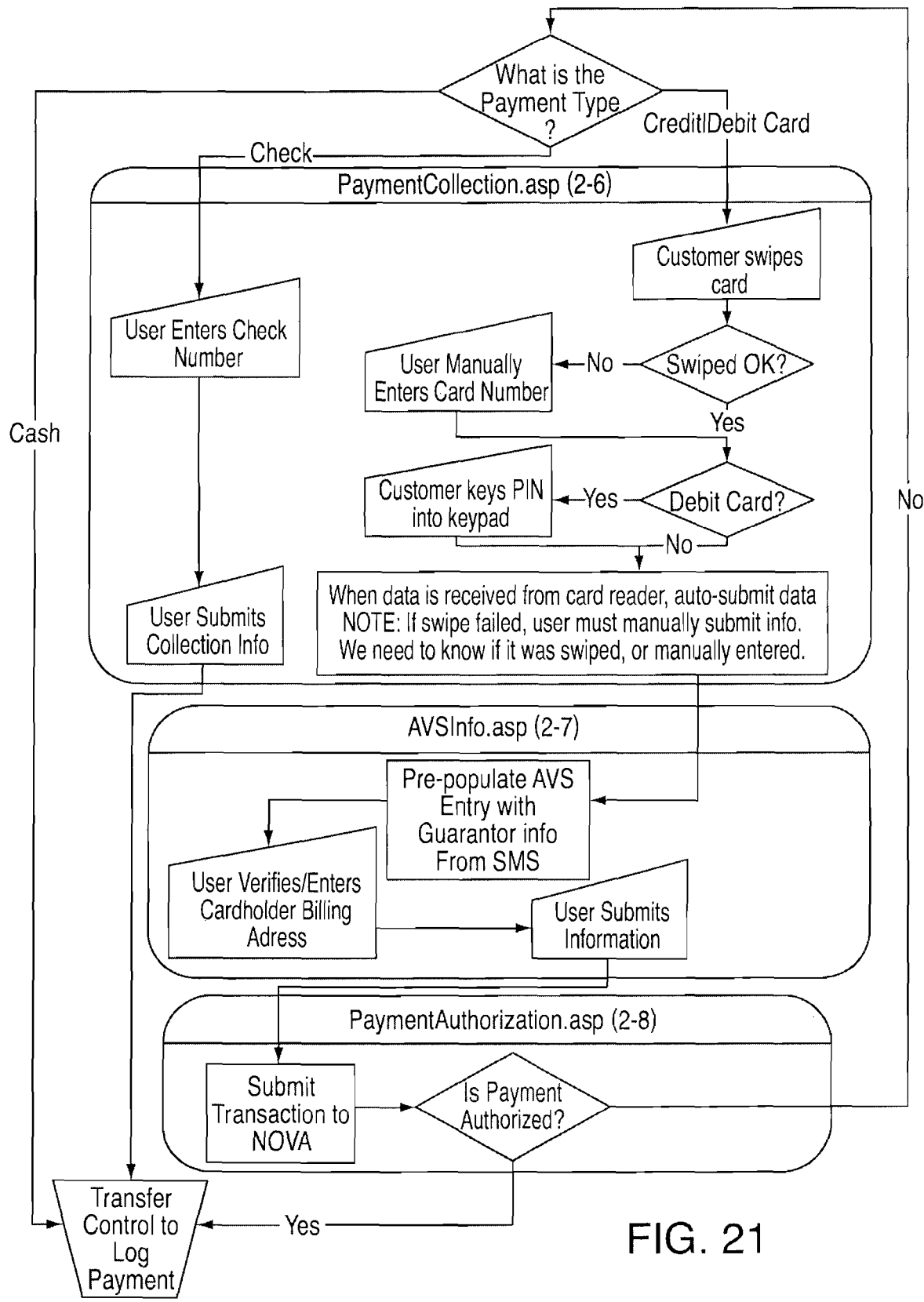
FIG. 21 is a block diagram which illustrates the operation of the Payment Collection function of the system.

FIG. 21 illustrates an exemplary payment collection in accordance with the present invention. Payment collection may include assessment of the payment type. It may be assessed that a check must be approved, and hence certain information must be collected from the customer in order to receive and insure eventual approval of, and collection on, the check. It may be assessed that a customer or another user, such as a facilitator or guardian, has swiped a credit or debit card. The data gained from the swipe of the card may generate an automated approval request from the card reader or keypad. The automated approver may receive a request from the approval location, such as from an approval server connected via the internet to the system of the present invention, for additional information, such as verification of a billing address or home phone number of the customer. This information may then be forwarded to the remote approver, and payment via the card may be approved.

Figure 22:
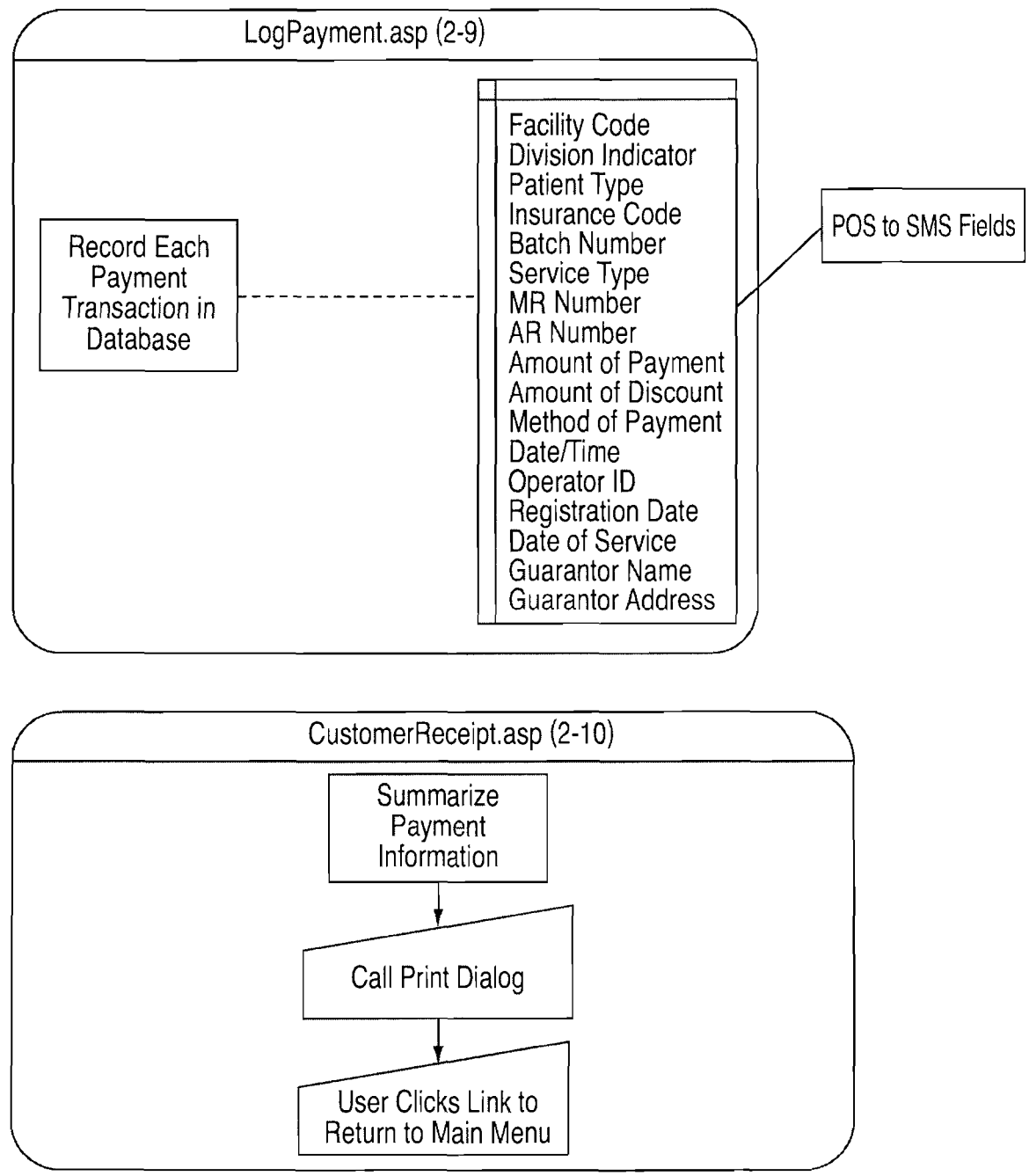
FIG. 22 is a block diagram which illustrates the operation of the Log Payment function of the system.

Further, as illustrated in FIG. 22, a payment, once made, such as being accepted or denied, may be logged. This payment log may be recorded in specified details to, for example, a storage location within or associated with the POS or administrator of the present invention. Further, a customer receipt incorporating selected portions of these payment log details may be generated at the POS upon receipt of payment, and/or upon receipt of past due payments, as discussed hereinabove.

Figure 23:
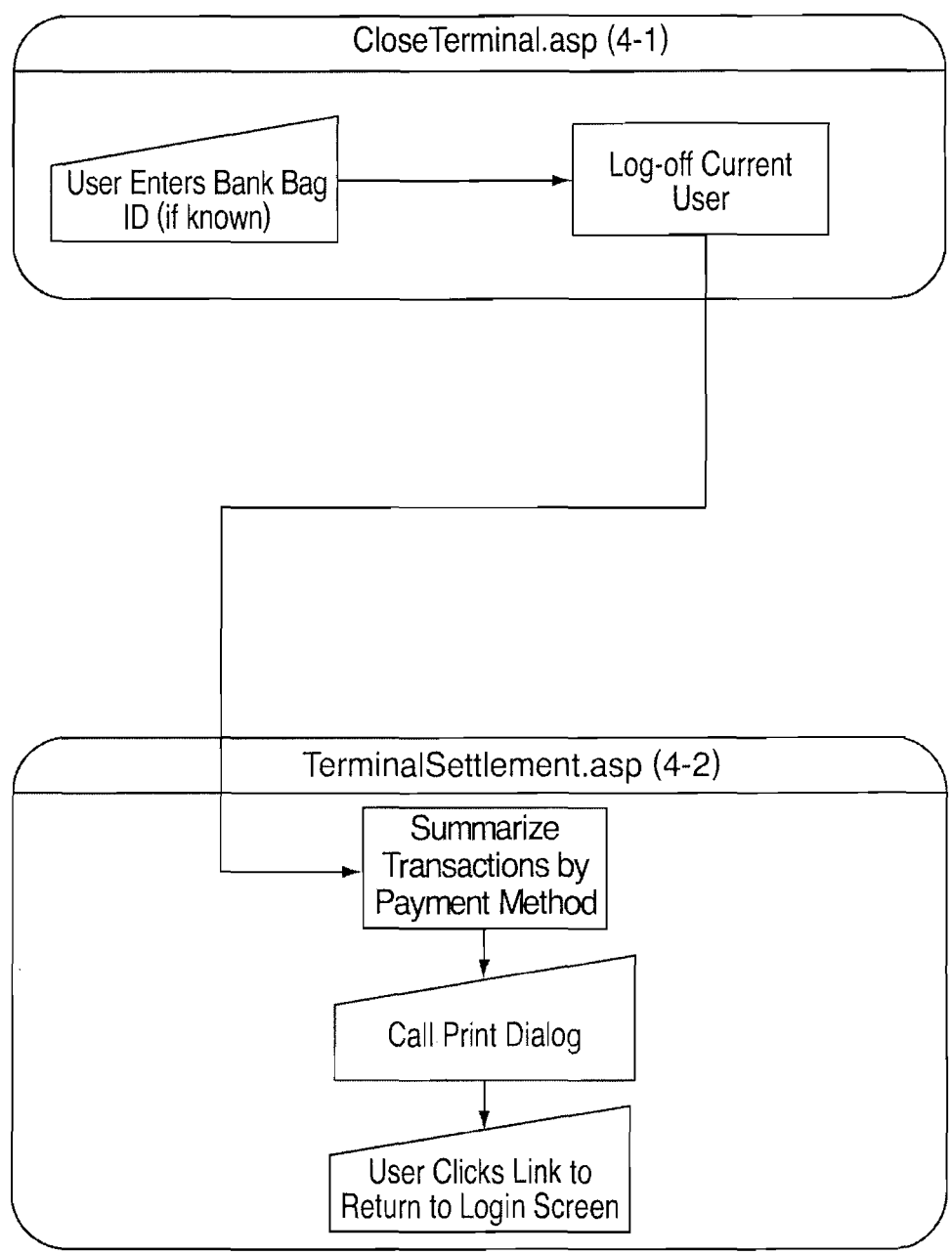
FIG. 23 is a block diagram which illustrates the operation of the Close Terminal function of the system.

As illustrated in FIG. 23, a user, such as the facilitator, may, if authorized to do so based upon user permissions, engage in terminal operations on terminals associated with the system and method of the present invention. For example, an authorized user may close or settle a terminal, either locally or remotely. A terminal may be terminated by logging off, or by shutting down the terminal. A terminal may be settled by summarizing, logging, or batching all transactions from that terminal.

Figure 24:
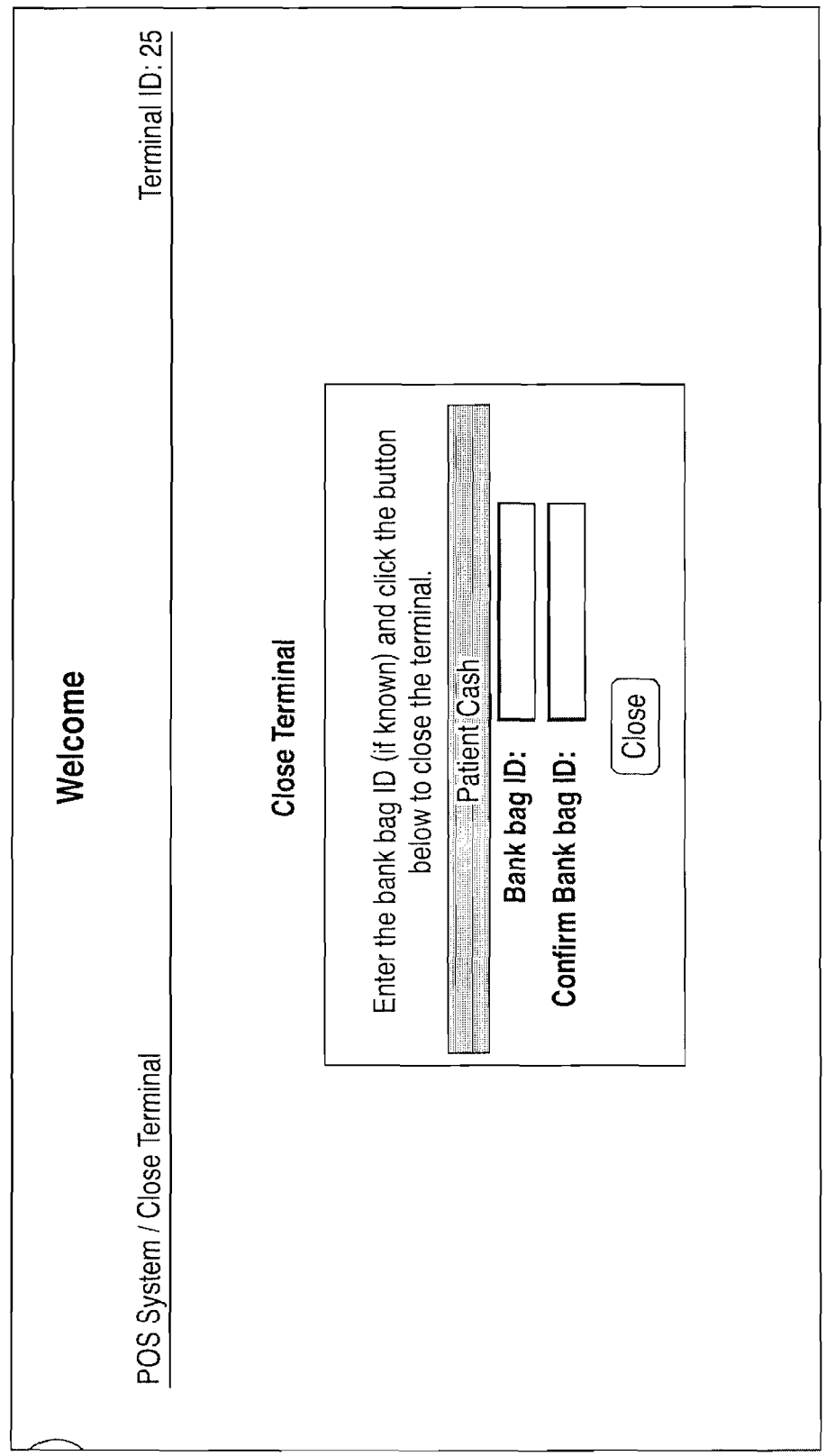
FIG. 24 is a screen shot which illustrates an aspect of an embodiment of the present invention.

Settling a terminal may include, for example, closing the terminal, as illustrated in FIGS. 24, 25, and 26. Closing a POS terminal may be analogous to closing a cash register out, for example, and thus may include settling cash payments made at the terminal, credit and debit payments made at the terminal or other payments made at the terminal. For example, the present invention may provide a continuous audit trail, whereby monies, and custody thereof, are tracked from being due until deposit.

Thus, upon closing of a POS terminal, monies due and paid may be differentiated by type, such as patient payments versus non-patient payments, which differentiation may be made based on accounting codes entered for each transaction, as discussed hereinabove. The settlement of differentiable payments may be made, for example, in separate windows, and may cause the generation of separate payment reports. Further, for example, different methods of payment, as evidenced by the batch payment data at the POS, will cause different information to be required to track each payment method type. For example, electronic payments, such as credit, debit, EFTs, or the like, may show approval codes or the like. Cash payments may request that a bank bag number be entered into which cash is placed, as illustrated in FIG. 24. The amount of cash placed into the bag may require reconciliation prior to terminal closing, and bags may be later combined in other areas of the service provider location, such as into larger bags, and those larger bag numbers are also tracked by the use of the present invention at each cashier terminal at which bags are dropped.

Further, the present invention may ensure entered cash bags exist and are approved for cash placement, and may track from where, and to where, and from whom and to whom, bags are passing. Additionally, bag numbers may be changed, and those changes may be tracked in the present invention. Thereby, a final manifest for daily, or hourly, or weekly, cash may be generated, and this manifest may be compared to bank deposit slips for final reconciliation. Consequently, lost, unreconciled, or undervalued bags may be flagged through the use of the present invention at any point, including upon deposit at a bank.

Figure 27:
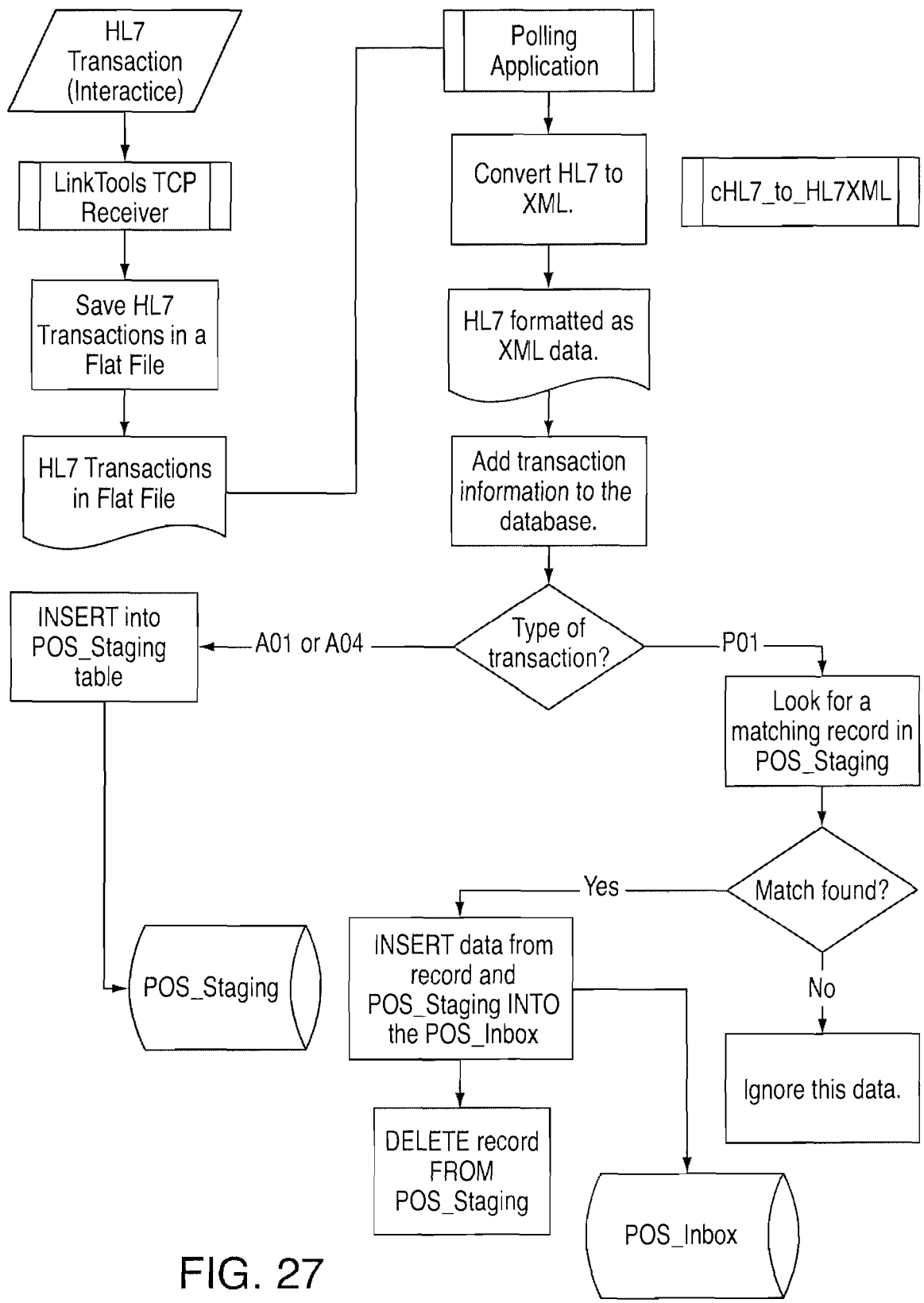
FIG. 27 is a block diagram which illustrates the operation of a first aspect of the Data Import function of the system.

As illustrated in FIG. 27, data importation may occur in the present invention via numerous methodologies. FIG. 27 specifically illustrates an embodiment wherein HL7 is imported to the method and system of the present invention. It will be apparent to those skilled in the art, as discussed hereinabove, that data importation may include: an accessing of external data, such as by user request or by customer action, such as by a card swipe identification; an assessment of the data type of that external data; a conversion, based on the data type assessed, to the language of choice for implementation of the system and method of the present invention; and a presentation of the translated conversion. Similarly, it will be apparent that data exportation may occur in a similar manner. In the exemplary embodiment of FIG. 27, an HL-7 conversion via a flat file is performed. The importer links, via a TCP or similar receiver, to the HL7 transaction, accepts the transaction as a flat file, polls until the flat file is accepted, and converts the HL7 flat file to XML. This importation methodology keeps all interactions of the application with externalities contained within one central location.

Figure 28:
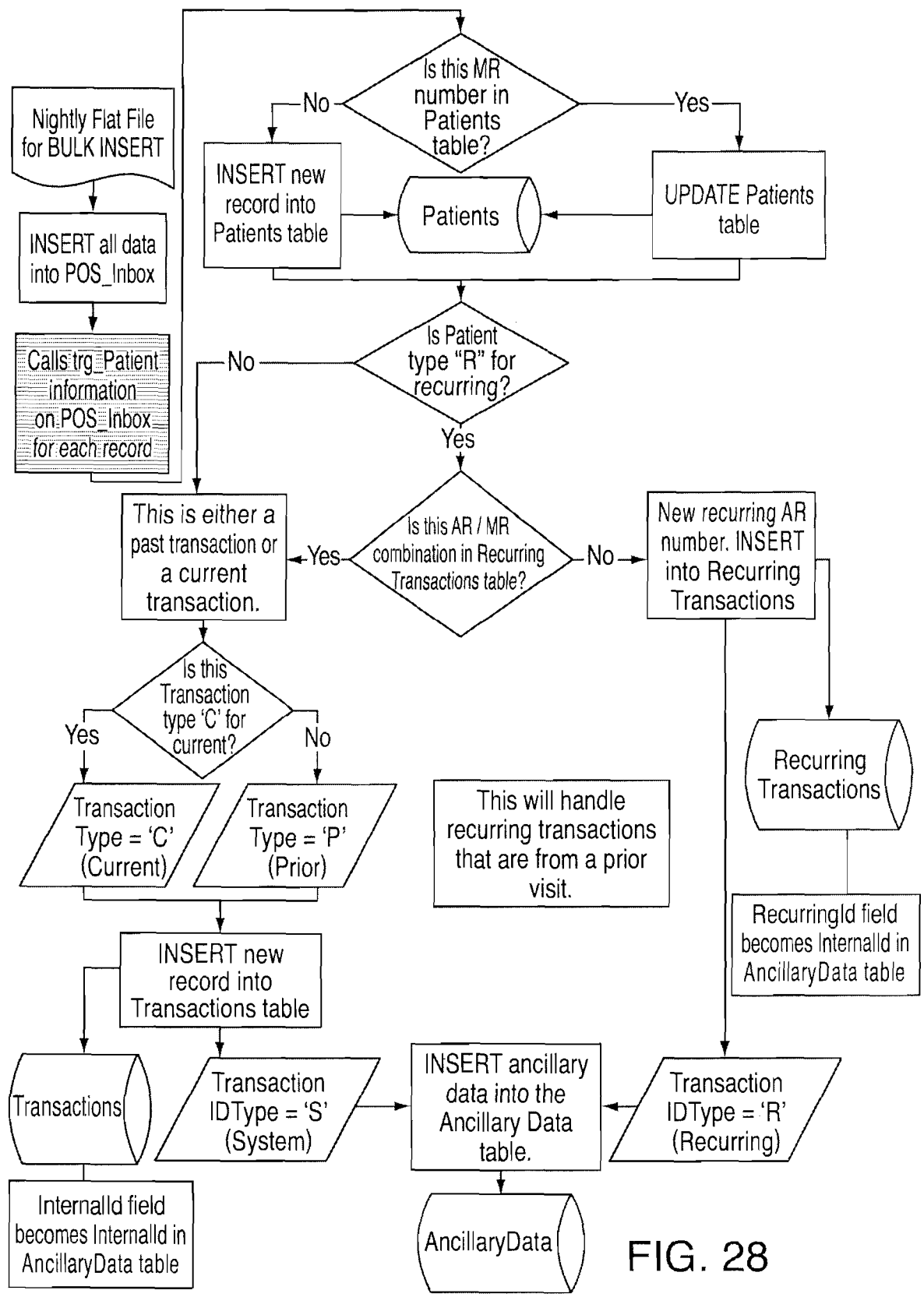
FIG. 28 is a block diagram which illustrates the operation of a second aspect of the Data Import function of the system.

FIG. 28 is a flow diagram more specifically illustrating an embodiment of data importation for use in the present invention. In the illustrated embodiment, a flat file is designated for bulk insertion at a predetermined interval, such as once daily, such as at night. A designated receiver, such as a POS_Inbox, at the receiver location may receive the batch flat file update and may parse to each applicable record, such as passing updated information on client A to the unique record of client A. Each patient record may thus be updated via the batched import files, and new records may be created automatically for new patients. Thus, both individual patient records and records of all past and existing patients may be updated by the batch flat file importation. The batch update may include transaction types, departments in which transactions occurred, payments, balance changes, and the like.

Thus, through the use of the system and method of the present invention, the data importation may be customizable, such as by using data from an existing, legacy, or input format into a standardized, genericized format. For example, for each type of data file that the system is to accept, a format file may be created associated to the POS, such as within or associated with the configuration files, that may be used to map the source data into the destination format, as discussed hereinabove.

Figure 29:
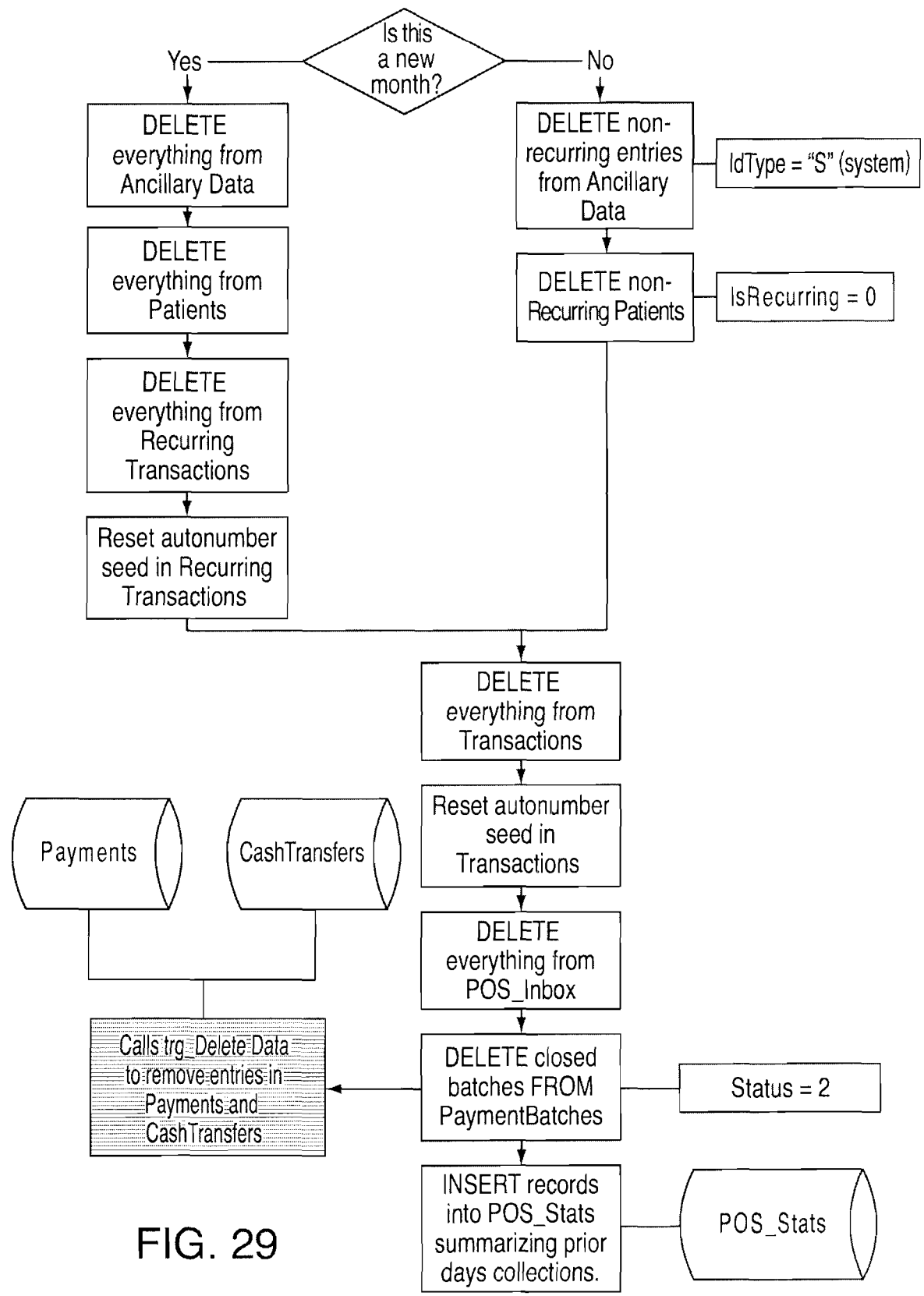
FIG. 29 is a block diagram which illustrates the operation of the Data Cleanup function of the system.

Further, as illustrated in the exemplary flow diagram of FIG. 29, the system and method of the present invention may perform maintenance of data at predetermined intervals, such as regular data cleanup and the like. For example, deletions of preselected data types, such as recurring patients and/or new patients, may be deleted, in whole or in part, at the start of each new month.

Figure 30:
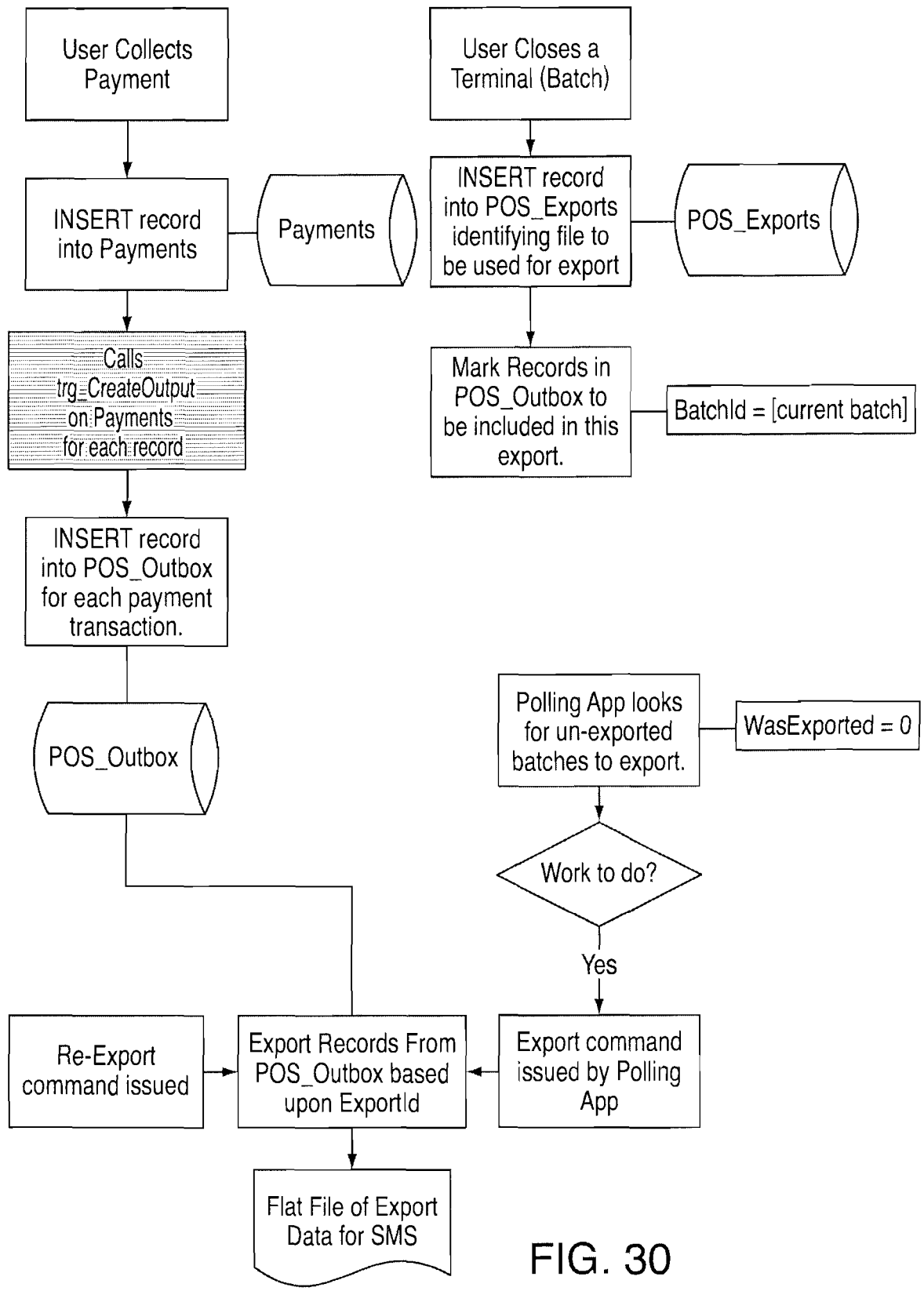
FIG. 30 is a block diagram which illustrates the operation of the Data Export function of the system.

FIG. 30 is a flow diagram illustrating the exportation of data by the use of an aspect of the present invention. Those skilled in the art will note that data exportation may be engaged similarly to a data importation transaction. More specifically, in the exemplary embodiment of FIG. 30, payments collected may be recorded, such as by a user, such as the facilitator, and inserted to a location, such as an outbox, upon collection. Records may be exported, such as in a flat file format, upon issuance of an exportation command, such as from a polling application.

Figure 31:
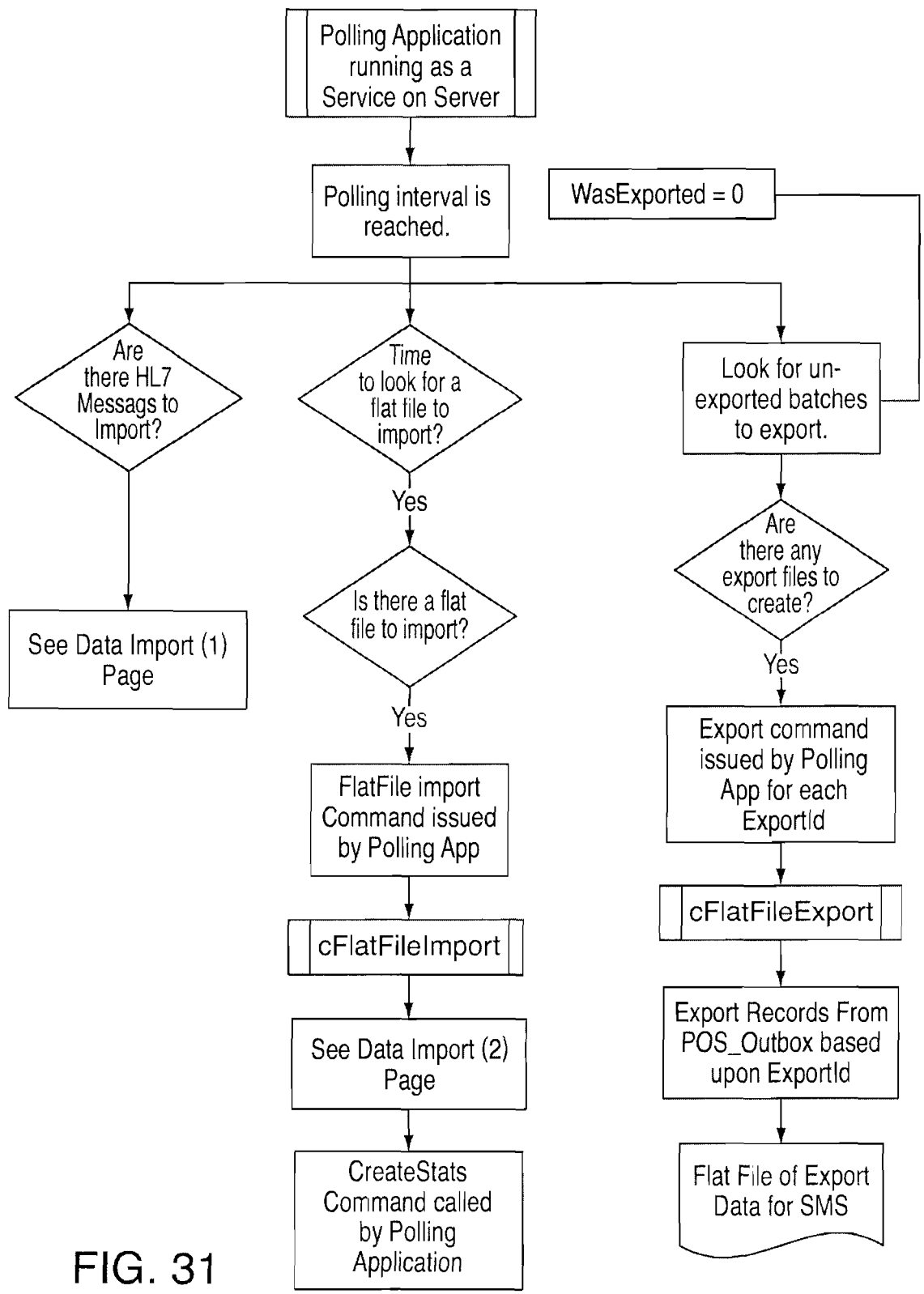
FIG. 31 is a block diagram which illustrates the operation of the Polling Application of the system.
Figure 32:
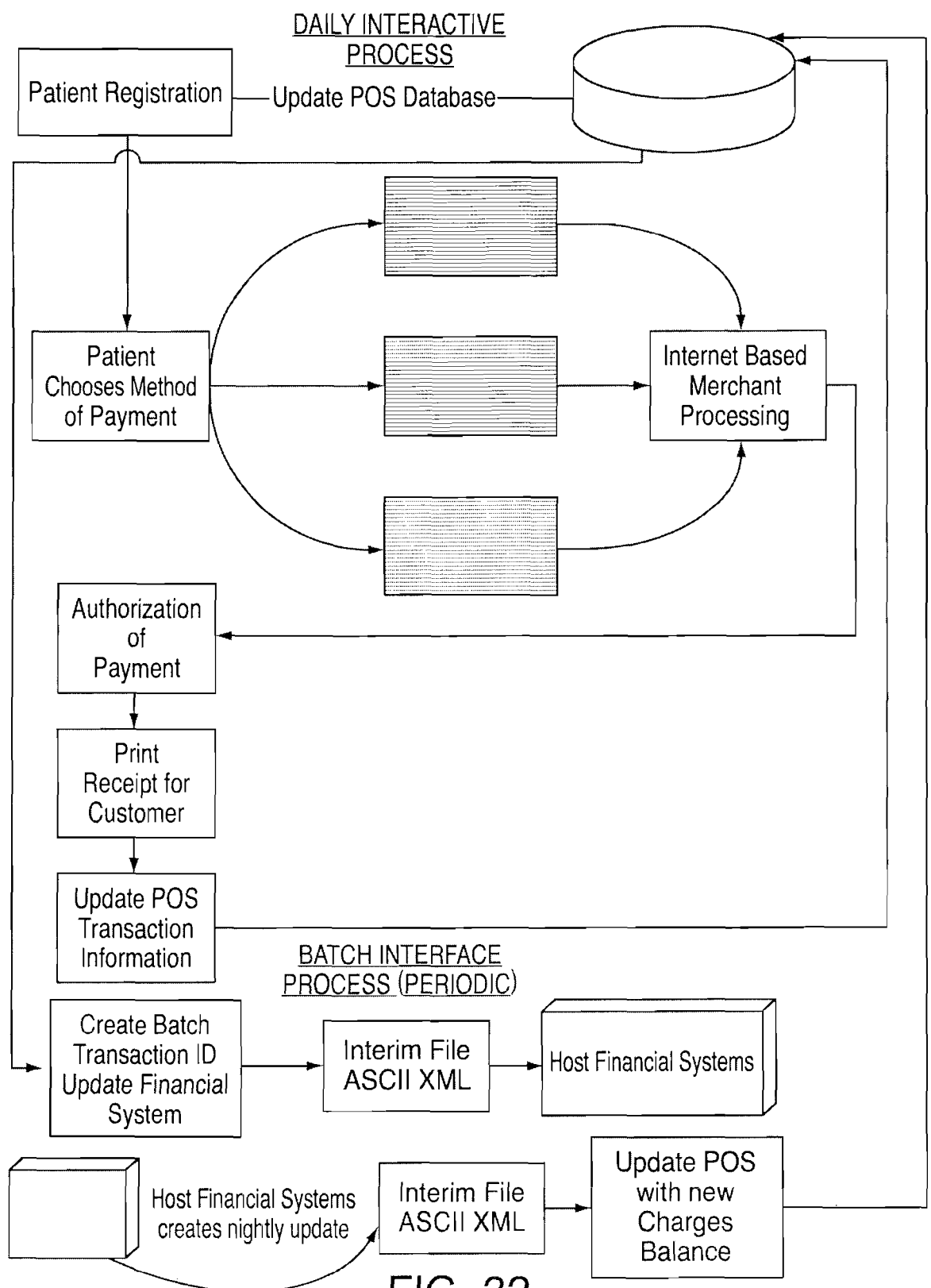
FIG. 32 is a block diagram which illustrates the operation of the Daily Interactive Process and Batch Interface Process (Periodic) of the system.
Figure 33:
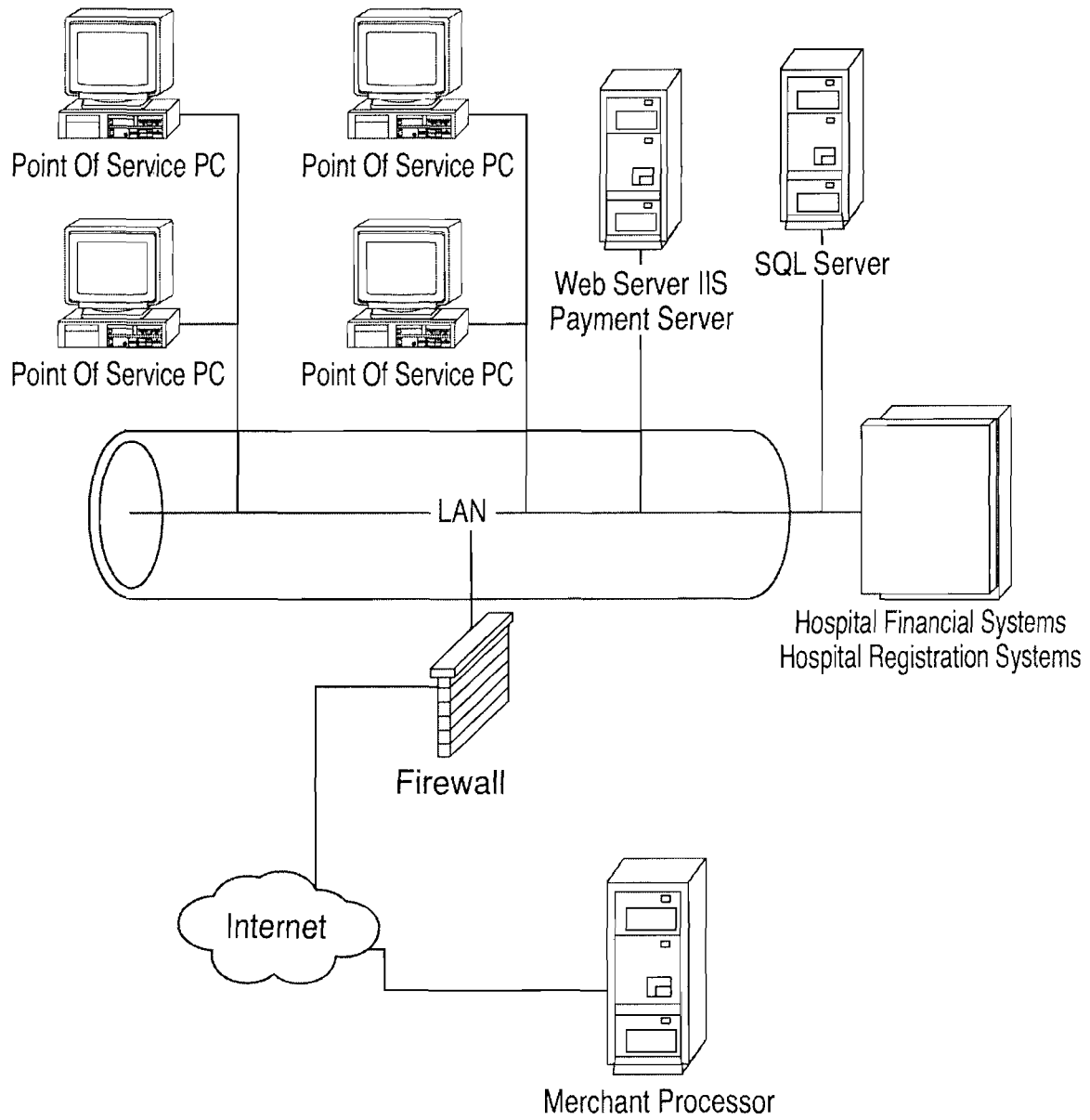
FIG. 33 is a block diagram which illustrates the general architecture of the system.

An exemplary polling application is illustrated in the flow diagram of FIG. 31. As illustrated, the polling application may be running on a central server. When the predetermined polling time or event is reached, the polling application may poll for data. The polling application may poll, for example, for particular types of data, such as HL7 data, or for genericized data, such as flat file data, that may be accepted as generic or genericized, such as by translation or conversion, or for data batched, for example. The polling application may read particular flags set that certain data types have been received and are responsive to the polling.

Further, as illustrated with respect to the exemplary embodiment of FIG. 31, if any portion of data import/export fails for any reason, POS payments and transactions can still occur while application aspects are down. For example, since POS transactions are handled separately, users can still collect money, and/or have credit cards authorized, and additionally users at other POSs remain unaffected. Further, once a problem is resolved, the polling application may pick up stored data from each POS, resulting in no system data loss. For example, when the aspect is eventually restarted, export files may have been automatically created, such as HL-7 and flat file transactions, and may simply have been queued up for export in the order they were received for importation, It will be apparent to those skilled in the art that the records of the present invention are associated with the users of the present invention based upon tracking of information regarding those users to allow that association, such as via one or more databases, such as relational databases. Information which may be tracked, and which thus may be requested prior to the implementation of a user in the system and method of the present invention, such as to set up a new user account, may include: (a) the number of locations in the provider's network, including name, location, number of campuses and size (such as total number of beds); (b) whether each of the locations have separate IT systems/staff; (c) whether there is a WAN in place; (d) the type of Internet connectivity, such as T-1, for example; (e) how many customer visits occur per month per location, and whether or not there are any peak times where visits are significantly higher than normal; (f) how many potential POS stations there are at each location; (g) the range of dollar amounts written off annually for non co-payment collection; (h) the range of dollar amounts written off annually for non self-pay collection; (i) the range of dollar amounts spent annually for collection agencies fees; (j) what current payment management and accounting systems already exist at each location; and/or (k) the facility's preferred server platform.

As discussed above, a facilitator may also have the ability to create and manage currency bags within and outside of the system. Currency bags may be used by a facilitator to handle cash receipts, including checks and other tender, which may not be suitable for electronic transactions/transfers. Currency bags may be used to transport cash receipts and to facilitate the deposit of such receipts in a bank or other secure location remote from the facilitator and/or collection site.

A facilitator may create a unique identifier for each currency bag and may produce both an electronic and physical identifier. For example, a physical identifier may take the form of a printed label which may, by way of further example, contain an identification means, such as a barcode and/or RFID tag. The unique identifier associated with the identification means may be similarly associated with the electronic currency bag ("e-bag"), and may be in the form of code within the system that is designated to be at least an e-bag with at least the unique currency bag identification associated therewith. As used herein, "bag" may mean either the physical currency bag, the physical identifier, an e-bag, and/or a grouping of said bag types. By way of example, a currency bag may be created by a facilitator and used by other facilitators and/or users of the system to collect cash receipts within a single POS, regardless of the number of collection points.

The contents of a currency bag may also be tracked and may be linked to a specific bag. This tracking may include "real-time" accounting of the bag's contents, including a running total of the contents' value and type. Tracking may also include the time of collection, "in" and "out" time stamps from collection points, as well as time to a central bag receiver and/or final deposit, system users, and payor information, for example.

Bags may also be collected from collections points and may be aggregated to ease deposit logistics and final accounting processes. For example, various collection points within a service facility may designate that any bags created during a defined time period may be collected and brought together at a central bag receiving location ("CBR"). Deposit of a bag at a CBR may allow for the bag(s) to be verified. Such a verification may include a comparison of the physical bag's contents to both the corresponding system e-bag the physical identifier attached to the physical bag. A receipt slip may then be generated which may detail the contents of the physical bag versus the e-bag and contents. A receipt may be printed for use by the handler of the bag and/or may be logged within the system.

Collection of the bags may occur at any defined time periods, such as, for example, three times a day, every six hours, or at or near the close of business (including the necessary time required for bag contents to be deposited in a bank for same-day posting). Collection may also occur by demand of a facilitator, whether local to or remote from the service facility. The collection of bags may include bags created at or for a particular collection point, and may also include bags created outside the current system. Such out-of-system bags may include bags used by the service facility and created for receiving payments made to persons not proximate to or authorized to use the present payment system. Other such bag items may include payments for facility use and out-of-coverage services, for example.

The collection of bags at a CBR may also allow for the correlation to each collection point of those bags collected over a certain period of time, which may be each day, month, and/or year, for example. This type of tracking may provide information related to frequency comparisons for bag usage/creation/contents volume, deposit types received, and/or collection time statistics, for example. This type of tracking may also allow for bag(s) to be created and tracked for a period of time without being collected and/or deposited during a defined cycle. For example, a bag may be created after the defined end-of-day pick-up period and may be tracked for pick-up during the following collection cycle. A bag(s) may also be intentionally held, but tracked, over several collection periods if, for example, the bag has very few contents. A threshold level for the bag(s) may be set within the system and may create efficiencies, such as by decreasing the number of created bags and/or the number of physical transitions a bag may undergo. A CBR may also create a new bag, which may include the contents and information related to at least a sub-set of collected bags, in preparation for transport for deposit.

A bag may be associated with a deposit manifest in preparation for transfer to a deposit location. A deposit location may include, for example, a bank or safe deposit box, while the transfer may be performed by any person, but preferably an armored courier. A deposit manifest may track the preparation, transfer and actual deposit of bags. For example, a consolidated bag at a CBR may be tracked as it is picked up by an armored courier and deposited with a bank. The information tracked may include the time each step is completed, the personnel involved, the identification and attributes of the bag(s) collected, and/or any confirmations provided by the bank, for example.

As described above, all bags may be tracked from creation to deposit (even if, as is contemplated, bags do not pass through a CBR). Thus, the contents of each bag may be tacked from the time of payment to deposit which may allow for a fully tracked and verified chain of custody. The information may also allow for reporting to the service facility and may include information relevant to various accounting ledgers and deposit reports.

As mentioned above, the present invention may allow for the processing of financial transactions outside the service facility's main operating tracking and processing means, such as, for example, non-patient-based transactions at a health care facility. Such transactions may include, by are not limited to, the use of reimbursement checks, payments and transfers of medical and non-medical supplies, petty cash, cash/check receipts from gift shops and cafeterias, employee check cashing benefit(s), parking receipts, promotional items such as movie tickets/theme park tickets, and/or the reconciliation of certain facility employee-based transactions, for example.

In an embodiment of the present invention, non-patient-based transactions may be posted on a service facility's accounting records, such as the general ledger, for example, and may be reconciled in a similar fashion to any other system transactions. For example, non-patient-based transactions may be initiated as a result of an employee at a POS reconciling their cash receipts discovering a discrepancy between the amount of money on hand versus the receipts from that day's transactions. To reconcile any differences, the employee or other system user may process a general ledger transaction to record the over/short condition of the cash drawer, for example.

With reference to the example above, the present invention may allow posting to the general ledger by a POS employee, such as a cashier, without providing full access to the accounting system. The present invention may allow for the loading of all or a subset of all general ledger codes utilized by the service facility for all financial transactions. If a transaction is processed, an automated posting function may allow the service facility's general ledger system to be updated. This may allow non-patient-based transactions to be posted to the general ledger versus being manually recorded and passed through an accounting department for entry and posting, as is done by service facilities today without the present invention. In this way, the POS employee does not need to be fully trained on complex general ledger accounting practices and software, and need not be provided access to highly confidential information but may nevertheless more efficiently complete the reconciliation of a the service facility's transactions.

If not otherwise stated herein, it may be assumed that all components and/or processes described heretofore may, if appropriate, be considered to be interchangeable with similar components and/or processes disclosed elsewhere in the specification. It should be appreciated that the systems and methods of the present invention may be configured and conducted as appropriate for any context at hand. The embodiments described hereinabove are to be considered in all respects only as illustrative and not restrictive. All changes which come within the meaning and range of equivalency of the claims hereinbelow are to be embraced within the scope thereof.

What is claimed:

1. A computerized, integrated point of service transaction management system, comprising:
   at least two points of service within at least one service facility;
   at least two computing terminals, each having associated therewith at least one processor, at least one at each of the at least two points of service at the at least one service facility;
   at least one computerized transaction database associated with each of the at least one processors for relationally and electronically tracking, within said at least one computerized transaction database, remotely from each of the at least one computing terminal;
      at least one physical bag containing at least one legal tender collected at one of the at least two computing terminals;
      at least one virtual bag correspondent to at least one bag identifier within said database, wherein the at least one bag identifier is associated in the at least one computerized transaction database with an originating one of the points of service, a real time location and a real time custody of the at least one physical bag, and an enumeration of each of the legal tender placed within the physical bag and collected at the originating one of the points of service, a payor of each of the legal tender, and a service associated with each of the legal tender; and
      at least one physical bag identifier correspondent to the physical bag and to the at least one bag identifier within the at least one computerized transaction database, wherein the at least one physical bag identifier is generated at a central one of the originating one of the points of service for physical association with the at least one physical bag and is subjected to an updated physical printed receipt at multiple locations that reflects the real time location and real time custody of the at least one physical bag.

2. The system of claim 1, wherein the service facility is a health care facility.

3. The system of claim 1, where the legal tender consists of one of the group selected from cash and checks.

4. The system of claim 1, wherein the central one of the originating one of the points of service is located within the at least one service facility.

5. The system of claim 1, wherein the at least one computerized transaction database comprises to an accounting system of the service facility.

6. The system of claim 1, wherein the at least one computerized transaction database is updated with a confirmation that the bag location is remote from the service facility.

7. The system of claim 1, wherein the at least one computerized transaction database is updated with a confirmation that the at least one legal tender was deposited in a bank.

* * * * *